US011538554B1

(12) United States Patent
Milenkovic et al.

(10) Patent No.: US 11,538,554 B1
(45) Date of Patent: Dec. 27, 2022

(54) NICK-BASED DATA STORAGE IN NATIVE NUCLEIC ACIDS

(71) Applicant: The Board of Trustees of the University of Illinois, Urbana, IL (US)

(72) Inventors: Olgica Milenkovic, Urbana, IL (US); Alvaro Gonzalo Hernandez, Champaign, IL (US); Seyed Kasra Tabatabaei, Urbana, IL (US); Huimin Zhao, Champaign, IL (US)

(73) Assignee: THE BOARD OF TRUSTEES OF THE UNIV OF ILLINOIS, Urbana, IL (US)

( * ) Notice: Subject to any disclaimer, the term of this patent is extended or adjusted under 35 U.S.C. 154(b) by 1135 days.

(21) Appl. No.: 16/136,066

(22) Filed: Sep. 19, 2018

Related U.S. Application Data
(60) Provisional application No. 62/560,245, filed on Sep. 19, 2017.

(51) Int. Cl.
  *G16B 30/00* (2019.01)
  *G16B 20/00* (2019.01)
  *G16B 50/00* (2019.01)

(52) U.S. Cl.
  CPC .............. *G16B 30/00* (2019.02); *G16B 20/00* (2019.02); *G16B 50/00* (2019.02)

(58) Field of Classification Search
  None
  See application file for complete search history.

(56) References Cited

U.S. PATENT DOCUMENTS

| 6,223,128 | B1 | 4/2001 | Allex et al. |
| 9,384,320 | B2 | 7/2016 | Church |
| 9,996,778 | B2 | 6/2018 | Church |
| 2004/0001371 | A1 | 1/2004 | Mansuripur et al. |
| 2005/0053968 | A1 | 3/2005 | Bharadwaj et al. |
| 2015/0261664 | A1 | 9/2015 | Goldman et al. |
| 2017/0141793 | A1 | 5/2017 | Strauss et al. |

(Continued)

FOREIGN PATENT DOCUMENTS

| WO | 2017189469 | 11/2017 |

OTHER PUBLICATIONS

Skinner et al. (Biocompatible Writing of Data into DNA, 2007, ournal of Bionanoscience, 1(1), p. 1-5) (Year: 2007).*

(Continued)

*Primary Examiner* — Olivia M. Wise
*Assistant Examiner* — Kaitlyn L Minchella
(74) *Attorney, Agent, or Firm* — McDonnell Boehnen Hulbert & Berghoff LLP

(57) ABSTRACT

Nick-based methods, devices, and systems for nick-based data storage in a deoxyribonucleic acid (DNA) sequence are disclosed. Digital information is encoded in a register of at least one copy of a double-stranded DNA sequence having a plurality of nickable positions. The data is translated into a sequence of values from a nick alphabet that is subsequently mapped to the plurality of nickable positions, and the DNA sequence is nicked according to the mapped values. Because the digital information is encoded as a series of nicked and non-nicked positions of a double-stranded DNA sequence, the nucleotide sequence of the DNA can be non-synthetic, or "native" DNA.

13 Claims, 19 Drawing Sheets

Specification includes a Sequence Listing.

(56) References Cited

U.S. PATENT DOCUMENTS

2018/0127804 A1  5/2018 Dean et al.

OTHER PUBLICATIONS

De Silva et al., New Trends of Digital Data Storage in DNA, 2016, BioMed Research International, p. 1-14 (Year: 2016).*
Wheeler et al., "The complete genome of an individual by massively parallel DNA sequencing," Nature 452(7189):872-76 (Apr. 2008).
Winfree, "DNA computing by self-assembly," The Bridge 33(4):31-38 (2003) Also available online at http://www.dna.caltech.edu/Papers/FOE 2003 final.pdf.
Wolf, "On codes derivable from the tensor product of check matrices," IEEE Transactions on Information Theory 11 (2):281-84 (1965).
Wood, "Applying error correcting codes to DNA computing (Abstract)" Proceedings of the 4th DIMACS International Meeting on DNA Based Computing, pp. 109-110 (1998).
Yazdi et al., "DNA-Based Storage: Trends and Methods" arXiv:1507.01611 published to arxiv.org on Jul. 6, 2015.
Yazdi et al., "A Rewritable, Random-Access DNA-Based Storage System," Sci. Rep. 5:14138 (Sep. 2015).
Yazdi et al., Supplementary Information for "A Rewritable, Random-Access DNA-Based Storage System" Sci. Rep. 5:14138 (Sep. 2015).
Yazdi et al., "Weakly Mutually Uncorrelated Codes" arXiv: 1601.08176; published to arxiv.org on Jan. 29, 2016.
Zerbino et al., "Velvet: algorithms for de novo short read assembly using de Bruijn graphs," Genome Res. 18(5):821-29 (May 2008).
Zhirnov et al., "Nucleic acid memory," Nat. Mater. 15:366-70 (2016).
Zuker, "Mfold web server for nucleic acid folding and hybridization prediction," Nucleic Acids Res. 31(13):3406-15 (2003) Web access at http://www.bioinro.rpi.edu/»zukerm/ma/.
Baranello et al., "DNA break mapping reveals topoisomerase II Activity genome-wide," Int. J. Mol. Sci. 15(7):13111-22 (2014).
Minsky, "Steps Toward Artificial Intelligence," Proceedings of the IRE (1961).
Qian & Winfree, "Scaling up Digital Circuit Computation with DNA Strand Displacement Cascades," Science 332 (6034):1196-1201 (2011).
Soloveichik et al., "DNA as a universal substrate for chemical kinetics," PNAS 107(12):5393-98 (2010).
Thachuk et al., "Leakless DNA Strand Displacement Systems," DNA Computing and Molecular Programming, Lecture Notes in Computer Science 9211:133-53 (2015).
Wang et al., "The Design Space of Strand Displacement Cascades with Toehold-Size Clamps," DNA Computing and Molecular Programming, Lecture Notes in Computer Science 10467:64-81 (2017).
Winfree, "Algorithmic self-assembly of DNA," Ph.D. dissertation, Thesis (Ph. D.)—California Institute of Technology (1998).
Yazdi, "Portable and Error-Free DNA-Based Data Storage," Scientific Reports 7(1):5011 (2017).
Johnson, "A new upper bound for error-correcting codes," Information Theory, IRE Transactions on 8(3):203-07 (1962).
Josefsson, "The Base16, Base32, and Base64 data encodings," IETF (2006).
Kannan et al., "More on reconstructing strings from random traces: insertions and deletions," Proc. IEEE Intl. Inform. Theory IEEE pp. 297-301 (2005).
Kaykobad, "Positive solutions of positive linear systems," Lin. Alg. and its App. 64:133-40 (Jan. 1985).
Khorana et al., "Syntheses of dideoxyribonucleotides," Journal of the American Chemical Society 79(4):1002-03 (1957).
Kim & Ma, "PSAR-Align: improving multiple sequence alignment using probabilistic sampling," Bioinformatics 30:1010-12 (2013).
King, "Bounds for DNA codes with constant GC-content," The Electronic Journal of Combinatorics 10(1):R33 (2003).
Kulkarni et al., "Nonasymptotic upper bounds for deletion correcting codes," IEEE Trans. on Info. Theory 59(8):5115-30 (Apr. 2013).
Kumar et al., "Mega3: integrated software for molecular evolutionary genetics analysis and sequence alignment," Briefings in bioinformatics 5(2):150-63 (2004).
Kiah et al., "Codes for dna storage channels," arXiv preprint arXiv:1410.8837, published to arxiv.org on Oct. 31, 2014.
Kiah et al., "Codes for dna sequence profiles," IEEE Trans. Inf. Theory 62, 3125-46 (2016).
Kim et al., "'Shotgun dna synthesis' for the high-throughput construction of large dna molecules," Nucleic acids research, p. gks546 (2012).
Kløve, "Error correcting codes for the asymmetric channel," Department of Pure Mathematics, University of Bergen, (1981).
Knuth, "Efficient balanced codes," Information Theory, IEEE Transactions on 32(1):51-53 (1986).
Kong et al., "Parallel gene synthesis in a microfluidic device," Nucleic acids research 35(8):e61 (2007).
Kosuri et al., "Scalable gene synthesis by selective amplification of dna pools from high-fidelity microchips," Nature biotechnology 28(12):1295-99 (2010).
Kosuri et al., "Large-scale de novo dna synthesis: technologies and applications," Nature methods 11(5):499-507 (2014).
Lee, H. et al., "A high-throughput optomechanical retrieval method for sequence-verified clonal dna from the ngs platform," Nature communications 6 (2015).
Lander et al., "Initial sequencing and analysis of the human genome," Nature 409(6822):860-921 (Feb. 2001).
Laure et al., "Coding in 2D: using intentional disperity to enhance the information capacity of sequence-coded polymer barcodes," Angew. Chem. 128:10880-83 (2016).
Laver et al., "Assessing the performance of the Oxford Nanopore Technologies MinION," BDQ 3:1-8 (2015).
LeProust et al., "Synthesis of high-quality libraries of long (150mer) oligonucleotides by a novel depurination controlled process," Nucleic acids research 38(8):2522-40 (2010).
Letsinger et al., "Oligonucleotide synthesis on a polymer support1, 2," Journal of the American Chemical Society 87(15):3526-27 (1965).
Letsinger et al "Nucleotide chemistry, xiii. synthesis of oligothymidylates via phosphotriester intermediates," Journal of the American Chemical Society 91(12):3350-55 (1969).
Letsinger et al., "Synthesis of thymidine oligonucleotides by phosphite triester intermediates," Journal of the American Chemical Society 98(12):3655-61 (1976).
Levenshtein, "Binary codes capable of correcting deletions, insertions, and reversals," in Soviet physics doklady 10(8):707-10 (1966).
Li & Durbin, "Fast and accurate short read alignment with Burrows-Wheeler Transform," Bioinformatics 25:1754-60 (1992).
Li et al., "De novo assembly of human genomes with massively parallel short read sequencing," Genome Res. 20(2):265-72 (Feb. 2010).
Ma et al., "Dna synthesis, assembly and applications in synthetic biology," Current opinion in chemical biology 16(3):260-67 (2012).
Ma et al., "Error correction in gene synthesis technology," Trends in biotechnology 30(3):147-54 (2012).
Mansuripur et al., "Information storage and retrieval using macromolecules as storage media," University of Arizona Technical Report (2003).
Marathe et al., "On combinatorial DNA word design," J. Comput. Biol. 8:201-19 (2001).
Massey, "Optimum frame synchronization," Communications, IEEE Transactions on 20:115-19 (1972).
MATLAB source code https://github.com/smhty/MATLAB_MinION (2016).
Matzas et al., "High-fidelity gene synthesis by retrieval of sequence-verified dna identified using high-throughput pyrosequencing," Nature biotechnology 28(12):1291-94 (2010).
Mazumdar et al., "Coding for high-density recording on a 1-D granular magnetic medium," IEEE Trans. on Info. Theory 57(11):7403-17 (Jun. 2011).
McGregor et al., "Trace reconstruction revisited," ESA 2014, 689-700 (2014).

(56) References Cited

OTHER PUBLICATIONS

Medvedev et al., "Computability of models for sequence assembly," Algorithms in Bioinformatics; Springer pp. 289-301 (2007).
Michelson et al., "Nucleotides part xxxii. synthesis of a dithymidine dinucleotide containing a 3': 5'-internucleotidic linkage," Journal of the Chemical Society (Resumed), pp. 2632-2638 (1955).
Milane et al., "Using Tablet for visual exploration of second-generation sequencing data," Brief. Bioinform. 14, 193-202 (2013).
Milenkovic, "On the generalized Hamming weight enumerators and coset weight distributions of even isodual codes," Proceedings of the 2001 IEEE International Symposium on Information Theory (Jun. 29, 2001).
Milenkovic et al., "On the design of codes for DNA computing" Coding and Cryptography International Workshop, Revised Selected Papers, pp. 100-119 (Mar. 2005).
Milenkovic et al., "DNA codes that avoid secondary structures," Proc. IEEE Int. Symp. Inform. Theory (ISIT'05), Adelaide, Australia, pp. 288-292 (Sep. 2005).
Milenkovic et al., "On the design of codes for DNA computing," In Coding and Cryptography, pp. 100-119 (Springer, 2006).
Mneimneh, "Computational Biology Lecture 20: RNA secondary structures," available online at engr.smu.edu/»saad/courses/cse8354/lectures/lecture20.pdf.
Molecular facts and figures available at https://www.idtdna.com/pages/docs/educational-resources/molecular-facts-and-figures.pdf?sfvrsn=4 (2016).
Morita et al., "On the construction of maximal prefix-synchronized codes," Information Theory, IEEE Transactions on 42:2158-66 (1996).
Nakamura et al., "Sequence-specific error profile of Illumina sequencers," Nucleic acids research p. gkr344, (2011).
Nussinov et al., "Fast algorithms for predicting the secondary structure of single stranded RNA," Proc. Natl. Acad. Sci. USA 77(11):6309-13 (1980).
Nuwaysir et al., "Gene expression analysis using oligonucleotide arrays produced by maskless photolithography," Genome research 12(11):1749-55 (2002).
Oleykowski et al., "Mutation detection using a novel plant endonuclease," Nucleic acids research 26(20):4597-602 (1998).
"Overlap Extension Polymerase Chain Reaction"—Wikipedia article https://en.wikipedia.org/wiki/Overlap_extension_polymerase_chain_reaction (retrieved Nov. 15, 2016).
Packer, "CRISPR and Cas9 for flexible genome editing," Technical report. (2014) Available at: www.idtdna.com/pages/products/genes/gblocks-gene-fragments/decoded-articles/decoded/2013/12/13/crispr-and-cas9-for-flexible-genome-editing (retrieved Jan. 1, 2015).
Paluncic et al., "A note on non-binary multiple insertion/deletion correcting codes," in IEEE Information Theory Workshop (2011).
Pease et al., "Light-generated oligonucleotide arrays for rapid dna sequence analysis," Proceedings of the National Academy of Sciences 91(11):5022-26 (1994).
Pevzner et al., "Towards DNA sequencing chips," in Mathematical Foundations of Computer Science 1994. Springer, pp. 143-58 (1994).
Pevzner et al., "An Eulerian path approach to DNA fragment assembly," Proc. Natl. Acad. Sci. U.S.A. 98(17):9748-53 (Aug. 2001).
Quan et al., "Parallel on-chip gene synthesis and application to optimization of protein expression," Nature biotechnology 29(5):449-52 (2011).
Reed et al., "Polynomial codes over certain finite fields," Journal of the society for industrial and applied mathematics 8(2):300-04 (1960).
Reese, "Oligo-and poly-nucleotides: 50 years of chemical synthesis," Organic & biomolecular chemistry 3(21):3851-68 (2005).
Richardson et al., "The capacity of low-density parity-check codes under message-passing decoding," IEEE Trans. on Info. Theory 47(2):599-618 (Aug. 2002).
Ross et al., "Characterizing and measuring bias in sequence data," Genome Biol. 14(5):R51 (May 2013).
Rouillard et al., "Oligoarray 2.0: design of oligonucleotide probes for DNA microarrays using a thermodynamic approach," Nucleic acids research 31:3057-62 (2003).
Roy et al., "Synthesis of dna/rna and their analogs via phosphoramidite and h-phosphonate chemistries," Molecules 18(11):14268-84 (2013).
Ruskey et al., "De Bruijn sequences for fixed-weight binary strings," SIAM Journal on Discrete Mathematics, 26(2):605-17 (2012).
Rykov et al., "DNA sequences and quaternary cyclic codes," Proc. IEEE Int. Symp. Inform. Theory (ISIT'01), Washington DC, p. 248 (Jun. 2001).
Saaem et al., "Error correction of microchip synthesized genes using surveyor nuclease," Nucleic acids research, p. gkr887 (2011).
Sala et al., "Exact reconstruction from insertions in synchronization codes," arXiv preprint, arXiv:1604.03000 (2016).
Sanger et al., "DNA sequencing with chain-terminating inhibitors," Proc. Natl. Acad. Sci. U.S.A. 74(12):5463-67 (Dec. 1977).
Schoeny et al., "Codes for correcting a burst of deletions or insertions," arXiv preprint, arXiv:1602.06820 (2016).
Schulman, "Asymptotically good codes correcting insertions, deletions, and transpositions," IEEE transactions on Information theory 45(7):2552-57 (1999).
Schuster, "Next-generation sequencing transforms today's biology," Nature methods 5:16-18 (2008).
Schwartz et al., "Accurate gene synthesis with tag-directed retrieval of sequence-verified dna molecules," Nature methods 9(9):913-15 (2012).
Shipman et al., "CRISPR-Cas encoding of a digital movie into the genomes of a population of living bacteria," Nature 547(7663):345-49 (Jul. 2017).
Simpson et al., "ABySS: a parallel assembler for short read sequence data," Genome Res. 19(6):1117-23 (Jun. 2009).
Simpson et al., "Efficient de novo assembly of large genomes using compressed data structures," Genome Res. 22(3):549-56 (Mar. 2012).
Singh-Gasson et al., "Maskless fabrication of light-directed oligonucleotide microarrays using a digital micromirror array," Nature biotechnology 17(10):974-78 (1999).
Sinha et al., "Polymer support oligonucleotide synthesis xviiil. 2): use of cyanoethyi-n, ndialkylamino-/n-morpholino phosphoramidite of deoxynucleosides for the synthesis of dna fragments simplifying deprotection and isolation of the final product," Nucleic Acids Research 12(11):4539-57 (1984).
Sloane, "On single-deletion-correcting codes," Codes and Designs, de Gruyter, Bedin, pp. 273-291 (2002).
Smith et al., "Removal of polymerase-produced mutant sequences from per products," Proceedings of the National Academy of Sciences 94(13):6847-50 (1997).
Sok et al., "Lattice based codes for insertion and deletion channels," IEEE Int. Symp. Inf. Theory 2013, 684-88 (2013).
Stanley, "Enumerative combinatorics," Cambridge university press 1. (2011).
Steinbock et al., "Probing the size of proteins with glass nanopores," Nanoscale 6:14380-87 (2014).
Stemmer et al., "Single-step assembly of a gene and entire plasmid from large numbers of oligodeoxyribonucleotides," Gene 164(1):49-53 (1995).
Stojanovic et al., "A deoxyribozyme-based molecular automaton," Nature Biotechnology 21:1069-74 (2003).
SvanstrÄom et al., "Bounds and constructions for ternary constant-composition codes," IEEE Trans. Inform. Theory 48(1)1101-11 (Jan. 2002).
Tal et al., "How to construct polar codes," IEEE Trans. on Info. Theory 59(10):6562-82 (Sep. 2013).
Tan et al., "Sets represented as the length-n factors of a word," in Combinatorics on Words Springer pp. 250-261 (2013).
Tavares, "A study of synchronization techniques for binary cyclic codes," Ph.D. dissertation, Thesis (Ph. D.)—McGill University (1968).
Tian et al., "Accurate multiplex gene synthesis from programmable dna microchips," Nature 432(7020):1050-54 (2004).
Tian et al., "Advancing high-throughput gene synthesis technology," Molecular BioSystems 5(7):714-22 (2009).

(56) References Cited

OTHER PUBLICATIONS

Till et al., "Mismatch cleavage by single-strand specific nucleases," Nucleic Acids Research 32(8):2632-41 (2004).
Tsaftaris et al., "DNA computing from a signal processing viewpoint," IEEE Signal Processing Magazine, pp. 100-106 (Sep. 2004).
Tzeng et al., "On extending Goppa codes to cyclic codes," IEEE Trans. Inform. Theory 21:712-16 (Nov. 1975).
Ukkonen, "Approximate string-matching with q-grams and maximal matches," Theoretical computer science 92(1):191-11 (1992).
Varshamov, "A class of codes for asymmetric channels and a problem from the additive theory of numbers," IEEE Trans. Inform. Theory 19(1):92-95 (1973).
Vilenchik, "Endogenous dna double-strand breaks: production, fidelity of repair, and induction of cancer," Proceedings of the National Academy of Sciences 100(22):12871-76 (2003).
Wallace, "The JPEG still picture compression standard," IEEE Transactions on Consumer Electronics 38:18-34 (1992).
Wan et al., "Error removal in microchip-synthesized dna using immobilized muts," Nucleic acids research, p. gku405 (2014).
Waterston et al., "Initial sequencing and comparative analysis of the mouse genome," Nature 420(6915):520-62 (Dec. 2002).
Duda et al., "Fundamental bounds and approaches to sequence reconstruction from nanopore sequencers," preprint available at http://arXiv.org/abs/1601.02420 (2016).
Edgar, MUSCLE: multiple sequence alignment with high accuracy and high throughput, Nucleic Acids Res. (32):1792-97 (2004).
Enghiad & Zhao, "Programmable DNA-Guided Artificial Restriction Enzymes," ACS Synth Biol. 6(5):752-57 (Feb. 2017).
Erlich & Zielinski, "Capacity-approaching DNA storage," preprint available at http://arXiv.org/abs/cs/0701166 (2007).
Erlich & Zielinski, "DNA Fountain enables a robust and efficient storage architecture," Science 355(6328):950-54 (Mar. 2017).
Farnoud et al., "Error-correction in flash memories via codes in the Ulam metric," IEEE Trans. Inform. Theory 59(5):3003-20 (2013).
Farnoud et al., "Multipermutation codes in the Ulam metric for nonvolatile memories," Selected Areas in Communications IEEE Journal on 32(5):919-32 (2014).
Fazeli et al., "Generalized Sphere Packing Bound," available at http://arxiv.org/abs/1401.6496 (2014).
Feng et al., "Identification of Single Nucleotides in MoS2 Nanopores," arXiv preprint, arXiv:1505.01608 (2015).
Feynman, "There's Plenty of Room at the Bottom," Caltech, Pasadena Lecture (Dec. 1959).
Fodor et al., "Light-directed, spatially addressable parallel chemical synthesis," Science 251:767-73 (1991).
Froehler et al., "Synthesis of dna via deoxynudeoside h-phosphonate intermediates," Nucleic Acids Research 14(13):5399-407 (1986).
Fuhrmann et al., "Removal of mismatched bases from synthetic genes by enzymatic mismatch cleavage," Nucleic acids research 33(6):e58 (2005).
Gaborit et al., "Linear constructions for DNA codes," Theoretical Computer Science 334(1-3):99-113 (Apr. 2005).
Gabrys et al., "Graded bit-error-correcting codes with applications to flash memory," IEEE Transactions on Information Theory 59(4):2315-27 (2013).
Gabrys et al., "Asymmetric lee distance codes for dna-based storage," arXiv preprint arXiv:1506.00740, published to arxiv.org on Jun. 2, 2015.
Gabrys et al., "Codes in the Damerau Distance for Deletion and Adjacent Transposition Correction" arXiv:1601.06885, published to arxiv.org on Sep. 6, 2016.
Gallager, "Low-density parity-check codes,Information Theory" IRE Transactions on 8(1):2128, (1962).
Gao et al., "In situ synthesis of oligonucleotide microarrays," Biopolymers 73(5):579-96 (2004).
Garegg et al., "Nucleoside h-phosphonates. iii. chemical synthesis of oligodeoxyribonucleotides by the hydrogenphosphonate approach," Tetrahedron letters 27(34):4051-54 (1986).

GBlocks (TM) Gene Fragments Cloning Protocols http://www.idtdna.com/pages/docs/synthetic-biology/gblocks-user-guide.pdf (retrieved Nov. 15, 2016).
Ghindilis et al., "Combimatrix oligonucleotide arrays: genotyping and gene expression assays employing electrochemical detection," Biosensors and Bioelectronics 22(9):1853-60 (2007).
Gibson, "Synthesis of dna fragments in yeast by one-step assembly of overlapping oligonucleotides," Nucleic acids research, p. gkp687 (2009).
Gibson et al., "Chemical synthesis of the mouse mitochondrial genome," nature methods 7(11):901-03 (2010).
Gilbert, "A comparison of signalling alphabets," Bell System Technical Journal 31(3):504-22 (1952).
Gilbert, "Synchronization of binary messages," Information Theory, IRE Transactions on 6:470-77 (1960).
Gilham et al., "Studies on polynucleotides, i. a new and general method for the chemical synthesis of the c5 internucleotidic linkage. syntheses of deoxyribo-dinucleotides1," Journal of the American Chemical Society 80(23):6212-22 (1958).
Gnerre et al. "High-quality draft assemblies of mammalian genomes from massively parallel sequence data," Proc. Natl. Acad. Sci U.S A. 108(4):1513-18 (2011).
Goda & Masaru, "The history of storage systems," IEEE 100:1433-40 (2012).
Goldman et al., "Towards practical, high-capacity, low-maintenance information storage in synthesized DNA," Nature 494(7435):77-80 (Jan. 2013).
Graham et al., "Lower bounds for constant weight codes," Information Theory, IEEE Transactions on 26(1):37-43 (1980).
Grass et al., "Robust chemical Preservation of Digital Information on DNA in Silica with Error-Correcting Codes," Angew. Chem. Int. Ed. Engl. 54(8):2552-55 (Feb. 2015).
Gray & Van Ingen, "Empirical measurements of disk failure rates and error rates," Preprint at http://arXIV.org/abs/cs/0701166 (2007).
Guibas et al., "Maximal prefix-synchronized codes," SIAM Journal on Applied Mathematics 35:401-18 (1978).
Hagiwara, "A short proof for the multi-deletion error correction property of Heiberg codes," IEICE Communications Express 5(2):49-51 (Jan. 25, 2016).
Hall et al., "644. nucleotides, part xli. mixed anhydrides as intermediates in the synthesis of dinucleoside phosphates," Journal of the Chemical Society (Resumed), pp. 3291-3296 (1957).
Hall, "Notes on Coding Theory (Chapter 5—Generalized Reed-Solomon Codes)" Department of Mathematics, Michigan State University available online at http://users.math.msu.edu/users/jhall/classes/codenotes/coding-notes.html (Jan. 2015 revision).
Hall, "Notes on Coding Theory (Chapter 6—Modifying Codes)" Department of Mathematics, Michigan State University available online at http://users.math.msu.edu/users/jhall/classes/codenotes/coding-notes.html (Jan. 2015 revision).
Hall, "Notes on Coding Theory (Chapter 7—Codes over Subfields)" Department of Mathematics, Michigan State University available online at http://users.math.msu.edu/users/jhall/classes/codenotes/coding-notes.html (Jan. 2015 revision).
Hall, "Notes on Coding Theory (Chapter 8—Cyclic Codes)" Department of Mathematics, Michigan State University available online at http://users.math.msu.edu/users/jhall/classes/codenotes/coding-notes.html (Jan. 2015 revision).
Hall, "Notes on Coding Theory (Chapter 9—Weight and Distance Enumeration)" Department of Mathematics, Michigan State University available online at http://users.math.msu.edu/users/jhall/classes/codenotes/coding-notes.html Jan. 2015 revision).
Helberg et al., "On multiple insertion/deletion correcting codes," Information Theory, IEEE Transactions on 48(1):305-08 (2002).
Heinrich, "Path decompositions," Le Matematiche 47(2):241-58 (1993).
Higuchi et al., "A general method of in vitro preparation and specific mutagenesis of dna fragments: study of protein and dna interactions," Nucleic acids research 16(15):7351-67 (1988).
Hof et al., "Capacity-achieving polar codes for arbitrarily permuted parallel channels," IEEE Trans. on Info. Theory 59(3):1505-16 (Mar. 2013).

(56) References Cited

OTHER PUBLICATIONS

Holenstein et al., "Trace reconstruction with constant deletion probability and related results," SODA 19:389-98 (2008).
Hughes et al., "Expression profiling using microarrays fabricated by an ink-jet oligonucleotide synthesizer," Nature biotechnology 19(4):342-47 (2001).
Jacquet et al., "Counting Markov types, balanced matrices, and Eulerian graphs," IEEE Trans. Inform. Theory 58(7):4261-72 (2012).
Jansen et al., "Identification of genes that are associated with dna repeats in prokaryotes," Molecular microbiology 43(6):1565-75 (2002).
Jiang et al., "Rank modulation for flash memories," IEEE Trans. Inform. Theory 55(6):2659-73 (2009).
Abualrub et al., "Construction of cyclic codes over GF(4) for DNA computing" Journal of the Franklin Institute 343:448-57 (2006).
Acharya et al., "On reconstructing a string from its substring compositions," Proc. IEEE Intl. Symp. Inform. Theory IEEE pp. 1238-42 (2010).
Acharya et al., "Quadratic-backtracking algorithm for string reconstruction from substring compositions," Proc. IEEE Intl. Symp. Inform. Theory IEEE pp. 1296-1300 (2014).
Adleman, "Molecular computation of solutions to combinatorial problems," Science 266:1021-24 (Nov. 1994).
Ahuja et al., "Network flows: theory, algorithms, and applications," Prentice Hall (1993).
Mderson et al., "On maximum Lee distance codes," J. of Discrete Mathematics (2013).
Astola, "The Theory of Lee-codes," Lappeenranta University of Technology, Department of Physics and Mathematics, Research Report (Jan. 1982).
Au et al., "Gene synthesis by a Icr-based approach: High-level production of leptin-I54 using synthetic gene inescherichia coli," Biochemical and biophysical research communications 248(1):200-03 (1998).
Bajic et al., "Distributed sequences and search process," Communications, IEEE International Conference 1:514-18 (2004).
Bajic et al., "A simple suboptimal construction of cross-bifix-free codes" Cryptography and Communications 6:27-37 (Aug. 2013).
Baldoni et al., "A user's guide for LattE integrate v1.7.2" retrieved from https://www.math.ucdavis.edu/~latte/software/packages/latte_current/manual_v1.7.2.pdf on Mar. 8, 2017 (Oct. 2014).
Bancroft et al., "Long-term storage of information in DNA," Science 293:1763-65 (2001).
Barg et al., "Codes in permutations and error correction for rank modulation," IEEE Trans. Inform. Theory 56(7):3158-65 (2010).
Barvinok, "A polynomial time algorithm for counting integral points in polyhedra when the dimension is fixed," Mathematics of Operations Research 19(4)769-79 (1994).
Batu et al., "Reconstructing strings from random traces," SODA 15:910-18 (2004).
Beaucage et al., "Deoxynucleoside phosphoramiditesa new class of key intermediates for deoxypolynucleotide synthesis," Tetrahedron Letters 22(20):1859-62 (1981).
Benenson et al., "An autonomous molecular computer for logical control of gene expression," Nature 429:423-29 (May 2004).
Berman et al., "Approximating maximum independent set in bounded degree graphs," In SODA 94:36571 (1994).
Binkowski et al., "Correcting errors in synthetic dna through consensus shuffling," Nucleic acids research 33(6):e55 (2005).
Bilotta et al., "A new approach to cross-bifix-free sets," IEEE Transactions on Information Theory 6(58):4058-63 (2012.
Blackburn, "Non-overlapping codes," arXiv preprint arXiv:1303.1026 (2013).
Blaum et al., "Error-correcting codes with bounded running digital sum," IEEE transactions on information theory 39:216-27 (1993).
Blawat et al., "Forward error correction for DNA data storage," Procedia Compu. Si. 80:1011-22 (2016).

Boneh et al., "Breaking DES using a molecular computer," Technical Report CS-TR-489-95, Department of Computer Science, Princeton University (1995).
Bornholt et al., "A dna-based archival storage system," Proceedings of the Twenty-First International Conference on Architectural Support for Programming Languages and Operating Systems ACM, pp. 637-649 (2016).
Borovkov et al., "High-quality gene assembly directly from unpurified mixtures of microarraysynthesized oligonucleotides," Nucleic acids research 38(19):e180 (2010).
Braich et al., "Solution of a 20-variable 3-SAT problem on a DNA computer," Science 296:492-502 (Apr. 2002).
Brakensiek et al., "Efficient low-redundancy codes for correcting multiple deletions," SODA 27:1884-92 (2016).
Breslauer et al., "Predicting DNA duplex stability from the base sequence," Proc. Natl. Acad. Sci. USA 83:3746-50 (1986).
Brill et al., "An improved error model for noisy channel spelling correction," Proceedings of the 38th Annual Meeting on Association for Computational Linguistics. Association for Computational Linguistics, pp. 286-293 (2000).
Bryksin et al., "Overlap extension PCR cloning: a simple and reliable way to create recombinant plasmids," Biotechniques 48:463 (2010).
Carr et al., "Protein-mediated error correction for de novo dna synthesis," Nucleic acids research 32(20):e162 (2004).
Chee et al., "Cross-bifix-free codes within a constant factor of optimality," Information Theory, IEEE Transactions on 59:4668-74 (2013).
Church et al., "Next-generation digital information storage in DNA," Science 337(6102):1628 (Aug. 2012).
Clote et al., "Computational Molecular Biology—An Introduction," Wiley Series in Mathematical and Computational Biology, New York (2000).
Cohen et al., "Dc-constrained error-correcting codes with small running digital sum," Information Theory, IEEE Transactions 37:949-55 (1991).
Compeau et al., "How to apply de Bruijn graphs to genome assembly," Nature biotechnology 29(11):987-91 (2011).
Cooke et al., "Polynomial construction of complex Hadamard matrices with cyclic core," Applied Mathematics Letters 12:87-93 (1999).
Cooper et al., "Generalized de Bruijn cycles," Annals of Combinatorics 8(1):13-25 (2004).
Cullina et al., "An improvement to levenshtein's upper bound on the cardinality of deletion correcting codes," IEEE Transactions on Information Theory 60(7):3862-70 (2014).
Damerau, "A technique for computer detection and correction of spelling errors," Commun. ACM 7(3):171-176 Available: http://doi.acm.org/10.1145/363958.363994 (Mar. 1964).
Davis, "Microvenus" Art Journal 55:70-74 (1996).
De Bruijn, "A combinatorial problem," Koninklijke Nederlandse Akademie v. Wetenschappen 49(49):758-64 (1946).
De Lind Van Wijngaarden et al., "Frame synchronization using distributed sequences," Communications, IEEE Transactions on 48(12):2127-38 (2000).
Delsarte, "An algebraic approach to the association schemes of coding theory," Doctoral dissertation, Universite Catholique de Louvain (1973).
Dolecek & Anantharam, "Repetition error correcting sets: explicit constructions and prefixing methods," SIDMA 23:2120-46 (2010).
Dormitzer et al., "Synthetic generation of influenza vaccine viruses for rapid response to pandemics," Science translational medicine 5(185):185ra68 (2013).
D'yachkov et al., "Exordium for DNA codes," J. Comb. Optim. 7(4):369-79 (2003).
D'yachkov et al., "New results on DNA codes," Proc. IEEE Int. Symp. Inform. Theory (ISIT'05), Adelaide, Australia, pp. 283-287 (Sep. 2005).

\* cited by examiner

SEQUENCE LISTING

<160> NUMBER OF SEQ ID NOS: 3

<210> SEQ ID NO 1
<211> LENGTH: 770
<212> TYPE: PRT
<213> ORGANISM: Pyrococcus furiosus

<400> SEQUENCE: 1

```
Met Lys Ala Lys Val Val Ile Asn Leu Val Lys Ile Asn Lys Lys Ile
1               5                   10                  15

Ile Pro Asp Lys Ile Tyr Val Tyr Arg Leu Phe Asn Asp Pro Glu Glu
            20                  25                  30

Glu Leu Gln Lys Glu Gly Tyr Ser Ile Tyr Arg Leu Ala Tyr Glu Asn
        35                  40                  45

Val Gly Ile Val Ile Asp Pro Glu Asn Leu Ile Ile Ala Thr Thr Lys
    50                  55                  60

Glu Leu Glu Tyr Glu Gly Glu Phe Ile Pro Glu Gly Glu Ile Ser Phe
65                  70                  75                  80

Ser Glu Leu Arg Asn Asp Tyr Gln Ser Lys Leu Val Leu Arg Leu Leu
                85                  90                  95

Lys Glu Asn Gly Ile Gly Glu Tyr Glu Leu Ser Lys Leu Leu Arg Lys
            100                 105                 110

Phe Arg Lys Pro Lys Thr Phe Gly Asp Tyr Lys Val Ile Pro Ser Val
        115                 120                 125

Glu Met Ser Val Ile Lys His Asp Glu Asp Phe Tyr Leu Val Ile His
130                 135                 140

Ile Ile His Gln Ile Gln Ser Met Lys Thr Leu Trp Glu Leu Val Asn
145                 150                 155                 160

Lys Asp Pro Lys Glu Leu Glu Glu Phe Leu Met Thr His Lys Glu Asn
                165                 170                 175

Leu Met Leu Lys Asp Ile Ala Ser Pro Leu Lys Thr Val Tyr Lys Pro
            180                 185                 190

Cys Phe Glu Glu Tyr Thr Lys Lys Pro Lys Leu Asp His Asn Gln Glu
        195                 200                 205

Ile Val Lys Tyr Trp Tyr Asn Tyr His Ile Glu Arg Tyr Trp Asn Thr
    210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
            260                 265                 270

Asn Ala Glu Gln Leu Glu Ser Asp Val Ala Lys Glu Ile Leu Glu Tyr
        275                 280                 285

Thr Lys Leu Met Pro Glu Glu Arg Lys Glu Leu Glu Asn Ile Leu
    290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
            340                 345                 350

Gln Leu Leu Leu Trp Thr Asn Tyr Ser Arg Lys Tyr Pro Val Ile Leu
        355                 360                 365
```

```
Pro Tyr Glu Val Pro Glu Lys Phe Arg Lys Ile Arg Glu Ile Pro Met
370                 375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
            405                 410                 415

Lys Lys Tyr Asn Ser Leu Ala Lys Lys Ala Arg Ser Thr Asn Glu Ile
            420                 425                 430

Gly Leu Pro Phe Leu Asp Phe Arg Gly Lys Lys Val Ile Thr Glu
            435                 440                 445

Asp Leu Asn Ser Asp Lys Gly Ile Ile Glu Val Val Glu Gln Val Ser
450                 455                 460

Ser Phe Met Lys Gly Lys Glu Leu Gly Leu Ala Phe Ile Ala Ala Arg
465                 470                 475                 480

Asn Lys Leu Ser Ser Glu Lys Phe Glu Ile Lys Arg Arg Leu Phe
                485                 490                 495

Asn Leu Asn Val Ile Ser Gln Val Val Asn Glu Asp Thr Leu Lys Asn
            500                 505                 510

Lys Arg Asp Lys Tyr Asp Arg Asn Arg Leu Asp Leu Phe Val Arg His
            515                 520                 525

Asn Leu Leu Phe Gln Val Leu Ser Lys Leu Gly Val Lys Tyr Tyr Val
530                 535                 540

Leu Asp Tyr Arg Phe Asn Tyr Asp Tyr Ile Ile Gly Ile Asp Val Ala
545                 550                 555                 560

Pro Met Lys Arg Ser Glu Gly Tyr Ile Gly Gly Ser Ala Val Met Phe
            565                 570                 575

Asp Ser Gln Gly Tyr Ile Arg Lys Ile Val Pro Ile Lys Ile Gly Glu
            580                 585                 590

Gln Arg Gly Glu Ser Val Asp Met Asn Glu Phe Phe Lys Glu Met Val
            595                 600                 605

Asp Lys Phe Lys Glu Phe Asn Ile Lys Leu Asp Asn Lys Lys Ile Leu
            610                 615                 620

Leu Leu Arg Asp Gly Arg Ile Thr Asn Asn Glu Glu Glu Gly Leu Lys
625                 630                 635                 640

Tyr Ile Ser Glu Met Phe Asp Ile Glu Val Val Thr Met Asp Val Ile
                645                 650                 655

Lys Asn His Pro Val Arg Ala Phe Ala Asn Met Lys Met Tyr Phe Asn
            660                 665                 670

Leu Gly Gly Ala Ile Tyr Leu Ile Pro His Lys Leu Lys Gln Ala Lys
            675                 680                 685

Gly Thr Pro Ile Pro Ile Lys Leu Ala Lys Arg Ile Ile Lys Asn
690                 695                 700

Gly Lys Val Glu Lys Gln Ser Ile Thr Arg Gln Asp Val Leu Asp Ile
705                 710                 715                 720

Phe Ile Leu Thr Arg Leu Asn Tyr Gly Ser Ile Ser Ala Asp Met Arg
            725                 730                 735

Leu Pro Ala Pro Val His Tyr Ala His Lys Phe Ala Asn Ala Ile Arg
            740                 745                 750

Asn Glu Trp Lys Ile Lys Glu Glu Phe Leu Ala Glu Gly Phe Leu Tyr
                755                 760                 765

Phe Val
770
```

```
<210> SEQ ID NO 2
<211> LENGTH: 450
<212> TYPE: DNA
<213> ORGANISM: Escherichia coli

<400> SEQUENCE: 2
actctgaatt tttgcggtgg tttcaagaag gattttttct ttaagagaaa ctatttcttt      60
caatccatca gaaatttttc ttttaatcac aacaccattt gcaggagatt ttatcaagct     120
catctctatt tttttcgca taaaatgtaa ttctctctaa aagtgttgat gcaagtggta     180
acggcgattg tatgtggtca acaaaatcag gaaataataa attaaatcgt tgctgcattg     240
ccaatggttg ttgccttata tagggtaaca acgttgaaaa accacatgtg atgatattgt     300
gatagttagc gatgccgggt ttgtatcgtg cctttttcatt tatttccagc ggtatagctg     360
ataaataatc ccttagtaca tcaggaacct tataaaaaaa cccgcgttct gcaaaccttt     420
ctcgataaaa gtgacaacca ctgagtaaac                                       450

<210> SEQ ID NO 3
<211> LENGTH: 449
<212> TYPE: DNA
<213> ORGANISM: Escherichia coli

<400> SEQUENCE: 3
gtgatagtta gcgatgccgg gtttgtatcg tgcctttttca tttatttcca gcggtatagc      60
tgataaataa tcccttagta catcaggaac cttataaaaa aacccgcgtt ctgcaaacct     120
ttctcgataa aagtgacaac cactgagtaa acagatcaat ggaagtaaat tccaattgtt     180
tattggattt gcccctatat ttccagacat ctgttatcac ttaacccatt acaagcccgc     240
tgccgcagat attcccgtgg cgagcgataa cccagcgcac tatgcggatg ccattcgtta     300
taatgctcga acgcctctgc aaggttcttt gctgccgtta acccgtctgg tttgggcatg     360
atactgatgt agtcacgctt tatcgttttc acgaagctct ctgctattcc gttactctcc     420
ggactccgca ccgccgtgtt cttcggttc                                        449
```

NICK-BASED DATA STORAGE IN NATIVE NUCLEIC ACIDS

CROSS-REFERENCE TO RELATED APPLICATIONS

This application is a continuation of and claims priority to U.S. patent application No. 62/560,245, filed Sep. 19, 2017, which is hereby incorporated by reference in its entirety.

STATEMENT REGARDING FEDERALLY SPONSORED RESEARCH OR DEVELOPMENT

This invention was made with government support under the DARPA Molecular Informatics Program. The government has certain rights in the invention.

SEQUENCE LISTING

The sequence listing submitted herewith, entitled "18-1205_ST25.txt" and 9 KB in size, is incorporated by reference in its entirety.

BACKGROUND

Modern data storage systems primarily rely on optical and magnetic media to record massive volumes of data that may be efficiently accessed, retrieved, and copied. As the amount of data created every day continues to increase, though, there is an ongoing need for reliable, high-density storage systems. Deoxyribonucleic acid (DNA) based storage platforms offer the possibility of achieving these goals. DNA molecules can potentially provide outstanding information integrity and ultra-high density, and can be read using portable sequencing technologies. Currently, DNA and its derivatives are the only molecules shown to enable random access to selected information content and large-scale amplification of data via a polymerase chain reaction (PCR).

However, the main obstacle to the practical deployment of DNA-based data storage systems is the exceptionally high cost of DNA synthesis. Short DNA strands used in several conventional solutions have blocklengths roughly equal to 100 base pairs (bps) and are relatively cheap to synthesize; nevertheless, their cost is still around 5-6 orders of magnitude higher than that of classical recording media such as tapes and disks. Another drawback associated with using such short blocklengths relates to random access: data blocks must be equipped with addresses, which are usually of length 15-20 bps, and typically require user data to be appropriately encoded. The encoding and address overhead may be as large as 30 bps, i.e., a 30% information loss for a 100-bp block. Moreover, near-optimal performance may be achieved only for sufficiently long blocklengths; encoding with short block lengths introduces excessive redundancy. And recently proposed "fountain approaches," which still require a large amount of redundant DNA blocks and rely on synthesized DNA, do not allow for random access nor for any form of computing because the blocks are not ordered.

SUMMARY

The embodiments herein provide methods, devices, and systems for nick-based data storage in a deoxyribonucleic acid (DNA) sequence. Digital information is encoded in a register of at least one copy of a double-stranded DNA sequence having a plurality of nickable positions. The data is translated into a sequence of values from a nick alphabet that is subsequently mapped to the plurality of nickable positions, and the DNA sequence is nicked according to the mapped values. Because the digital information is encoded as a series of nicked and non-nicked positions of a double-stranded DNA sequence, the nucleotide sequence of the DNA can be non-synthetic, or "native" DNA, which is abundant and readily available, and accordingly cost-effective. In some examples, data may be encoded in multiple "orthogonal" registers of native DNA (e.g., regions of length 450-bps taken from different regions of E. coli or from different bacteria such that they have very little sequence overlap).

Once data is encoded in this fashion, the nicked positions may be detected, e.g., by a sequencer, and mapped to a plurality of reference nickable positions of a reference sequence to determine a sequence of values from the nick alphabet. The sequence of values from the nick alphabet is translated into unencoded data. Additionally, single-stranded "toehold" regions of a DNA sequence, required for computational paradigms involving strand displacement but previously unattainable by synthetic means, can be formed by nicking. Toehold regions are further involved in the displacement of nicked positions of a DNA sequence: A first strand having a first nicked position is nicked at a second position, and the portion of the first strand bounded by the nicked positions is dissociated, providing a toehold for a DNA displacement strand. The first strand is nicked at a third position, and a displacement strand associates with the toehold, displaces the portion of the first strand bounded by the toehold and the third nicked position, and is ligated to the first strand of the DNA sequence at the first nicked position.

Particularly, a first example embodiment may involve a method. The method includes storing data by providing a register of at least one copy of a double-stranded DNA sequence, the DNA sequence having a plurality of nickable positions. The data is translated into a sequence of values from a nick alphabet, the alphabet comprising at least a first value and a second value. The first value of the alphabet indicates not to nick the DNA sequence, and the second value indicates to nick the DNA sequence. The sequence of values from the nick alphabet is mapped to the plurality of nickable positions, and one strand of the DNA sequence is nicked at each nickable position having a mapped value that indicates to nick the DNA sequence, providing an encoded register.

A second example embodiment may involve a method. The method includes reading a double-stranded DNA sequence of an encoded register by detecting one or more nicked positions of the DNA sequence. The nicked positions are mapped to a plurality of reference nickable positions of a reference sequence of the encoded register to determine a sequence of values from a nick alphabet. The nick alphabet includes a first value indicating that the DNA sequence was not nicked at a reference position and a second value indicating that the DNA sequence was nicked at a reference position. The sequence of values from the nick alphabet is translated into unencoded data.

A third example embodiment may involve a method. The method includes displacing a nick of a double-stranded DNA sequence of an encoded register by providing a DNA sequence, a first strand of the DNA sequence nicked at a first nicked position. The first strand of the DNA sequence is nicked at a second nicked position, and the portion of the first strand bounded by the first and second nicked positions is dissociated from the DNA sequence to provide a single-stranded portion of the DNA sequence. The first strand of the DNA sequence is nicked at a third nicked position separated from the first nicked position by the second nicked position. A DNA displacement strand is associated with the single-stranded portion of the DNA sequence, displacing from the DNA sequence the portion of the first strand bounded by the second nicked position and the third nicked position. The first strand of the DNA sequence and the DNA displacement strand are ligated at the first nicked position.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

The features, objects and advantages other than those set forth above will become more readily apparent when consideration is given to the detailed description below. Such detailed description makes reference to the following drawings, wherein.

Figure 1:
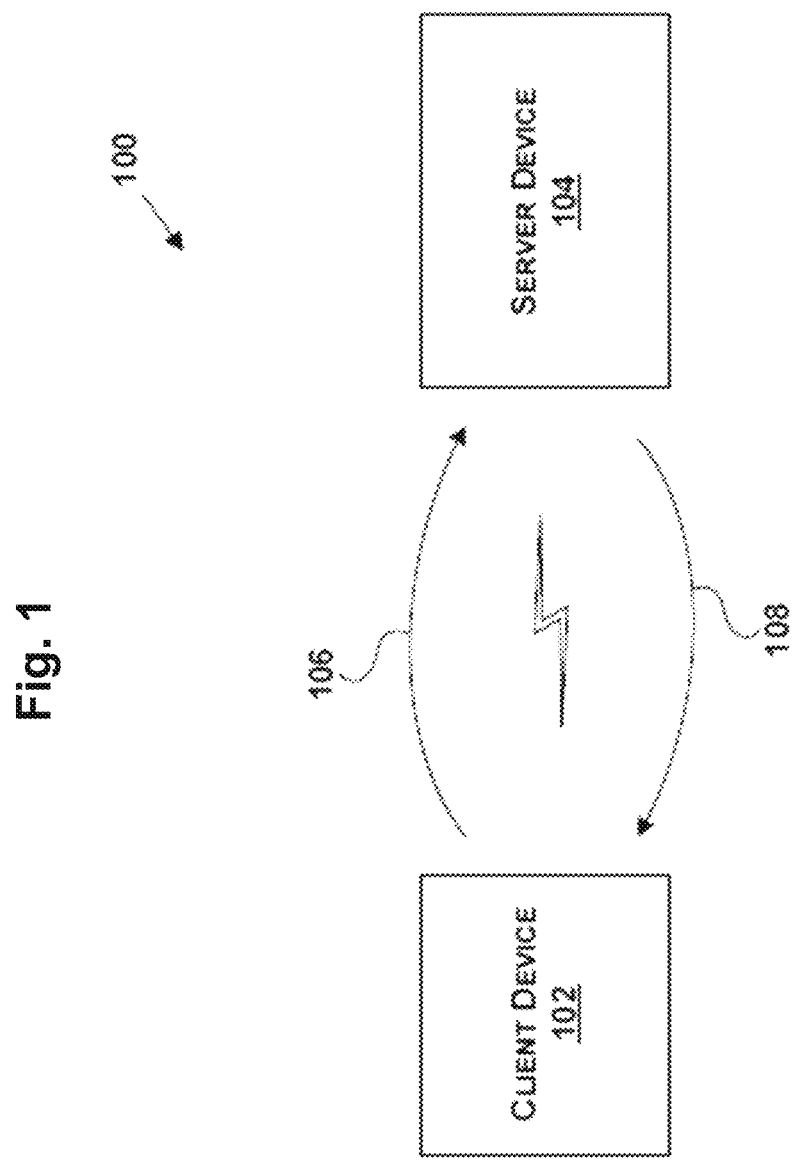
FIG. 1 is a high-level depiction of a client-server computing system, according to example embodiments.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

Example methods, devices, media, and systems are described herein. Other embodiments can be utilized, and other changes can be made, without departing from the scope of the subject matter presented herein. Thus, these example embodiments are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

As used herein, the words "example" and "exemplary" mean "serving as an example, instance, or illustration." Any embodiment or feature described herein as being an "example" or "exemplary" is not necessarily to be construed as preferred or advantageous over other embodiments or features. The term "optimization" as used herein should not be interpreted to require that the "optimal" or "best" solution to any problem is found. Instead, "optimization" refers to a process through which better results may be obtained.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Regardless of how they may be implemented, the embodiments herein may make use of one or more computing devices. These computing devices may include, for example, client devices under the control of users, and server devices that directly or indirectly interact with the client devices. For example, a user may use a client device to input a request to save or retrieve data. The client device may transmit the request to a server device. The server device may cause the data to be saved to or retrieved from a nucleic acid based storage system, as described herein. Such computing devices are described in the following section.

Example Computing Devices and Environments

FIG. 1 illustrates an example communication system 100 for carrying out one or more of the embodiments described herein. Communication system 100 may include computing devices. Herein, a "computing device" may refer to either a client device, a server device (e.g., a stand-alone server computer or networked cluster of server equipment), or some other type of computational platform.

Client device 102 may be any type of device including a personal computer, laptop computer, a wearable computing device, a wireless computing device, a head-mountable computing device, a mobile telephone, or tablet computing device, etc., that is configured to transmit data 106 to and/or receive data 108 from a server device 104 in accordance with the embodiments described herein. For example, in FIG. 1, client device 102 may communicate with server device 104 via one or more wireline or wireless interfaces. In some cases, client device 102 and server device 104 may communicate with one another via a local-area network. Alternatively, client device 102 and server device 104 may each reside within a different network, and may communicate via a wide-area network, such as the Internet.

Client device 102 may include a user interface, a communication interface, a main processor, and data storage (e.g., memory). The data storage may contain instructions executable by the main processor for carrying out one or more operations relating to the data sent to, or received from, server device 104. The user interface of client device 102 may include buttons, a touchscreen, a microphone, and/or any other elements for receiving inputs, as well as a speaker, one or more displays, and/or any other elements for communicating outputs.

Server device 104 may be any entity or computing device arranged to carry out the server operations described herein. Further, server device 104 may be configured to send data 108 to and/or receive data 106 from the client device 102.

Data 106 and data 108 may take various forms. For example, data 106 and 108 may represent packets transmitted by client device 102 or server device 104, respectively, as part of one or more communication sessions. Such a communication session may include packets transmitted on a signaling plane (e.g., session setup, management, and teardown messages), and/or packets transmitted on a media plane (e.g., text, graphics, audio, and/or video data).

Regardless of the exact architecture, the operations of client device 102, server device 104, as well as any other operation associated with the architecture of FIG. 1, can be carried out by one or more computing devices. These computing devices may be organized in a standalone fashion or in other arrangements.

Figure 2:
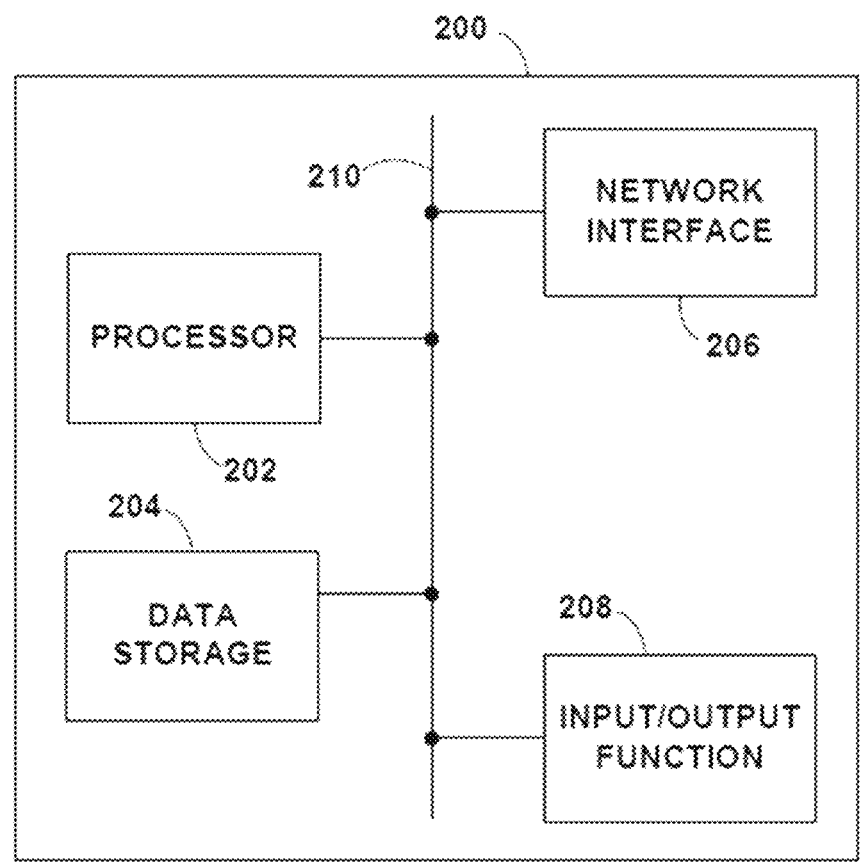
FIG. 2 illustrates a schematic drawing of a computing device, according to example embodiments.

FIG. 2 is a simplified block diagram exemplifying a computing device 200, illustrating some of the functional components that could be included in a computing device arranged to operate in accordance with the embodiments herein. Example computing device 200 could be a client device, a server device, or some other type of computational platform. For purpose of simplicity, this specification may equate computing device 200 to a server from time to time. Nonetheless, the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more CPUs, such as one or more general purpose processors and/or one or more dedicated processors (e.g., application specific integrated circuits (ASICs), digital signal processors (DSPs), network processors, etc.).

Data storage 204, in turn, may comprise volatile and/or non-volatile data storage and can be integrated in whole or in part with processor 202. Data storage 204 can hold program instructions, executable by processor 202, and data that may be manipulated by these instructions to carry out the various methods, processes, or operations described herein. Alternatively, these methods, processes, or operations can be defined by hardware, firmware, and/or any combination of hardware, firmware and software. By way of example, the data in data storage 204 may contain program instructions, perhaps stored on a non-transitory, computer-readable medium, executable by processor 202 to carry out any of the methods, processes, or operations disclosed in this specification or the accompanying drawings.

Network interface 206 may take the form of a wireline connection, such as an Ethernet, Token Ring, or T-carrier connection. Network interface 206 may also take the form of a wireless connection, such as IEEE 802.11 (Wifi), BLUETOOTH®, or a wide-area wireless connection. However, other forms of physical layer connections and other types of standard or proprietary communication protocols may be used over network interface 206. Furthermore, network interface 206 may comprise multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices.

Example DNA Structure and Sequencing

Sequencing may involve determining the order of nucleotides in a single- or double-stranded nucleic acid (NA) sequence, e.g., comprising RNA or DNA. Each nucleotide contains one base structure (or nucleobase) which may be adenine (A), guanine (G), cytosine (C), or thymine (T) for DNA. In RNA, thymine bases are replaced by uracil (U) bases.

A strand of DNA may include tens, hundreds, thousands, millions, or billions of nucleotides in a particular ordering. Complete DNA sequences, or genomes, of various organisms have been discovered via a group of techniques generically referred to as "sequencing." Rather than attempting to sequence an entire genome in a monolithic operation, relatively short blocks of DNA (e.g., a few hundred or a few thousand nucleotides) may be sequenced individually. The sequencing of the individual blocks may involve steps of amplification and electrophoresis.

Amplification refers to the copying of a block of DNA. Various amplification techniques may be used to make multiple copies of such a block from a small initial sample. For instance, polymerase chain reaction (PCR) is an amplification technique that can rapidly produce thousands of copies of a block.

Using PCR, the block containing the DNA sequencing target, primers (short single-stranded DNA fragments containing subsequences that are complimentary to the sequencing target), free nucleotides, and a polymerase are placed in a thermal cycler. Therein, the sequencing target undergoes one or more cycles of denaturation, annealing, and extension.

In the denaturation phase, the thermal cycler is set to a high temperature (e.g., about 98° C.), which breaks the hydrogen bonds between bases of the sequencing target. The results are two complementary single-stranded DNA molecules. In the annealing phase, the thermal cycler is set to a lower temperature (e.g., about 69° C.), which allows bonding of the primers to the single-stranded molecules. Once the primers are bonded to the appropriate locations of the single-stranded molecules, the extension phase begins. The thermal cycler is set to an intermediate temperature (e.g., a temperature between those used in the denaturation and annealing phases), and the polymerase binds complementary free nucleotides along the single-stranded molecules, effectively creating a copy of the original two-stranded DNA sequencing target.

These three phases repeat any number of times, creating an exponentially-growing number of copies of the original sequencing target. For example, in only a few hours, one million or more copies of the original sequencing target may be produced.

An initially popular method of DNA sequencing was the Sanger sequencing method. In order to facilitate sequencing the original sequencing target by this method, dideoxynucleotides (ddNTPs) are added to the free nucleotides. A ddNTP has the same chemical structure as the free nucleotides, but is missing a hydroxyl group at the 3' position (e.g., at the end of the molecule to which DNA polymerase incorporates the subsequent nucleotide). Consequently, if a ddNTP is incorporated into a growing complementary strand during the extension phase, it may act as a polymerase inhibitor because the missing hydroxyl group prevents the strand from being elongated. Because the incorporation of ddNTPs is random, when the polymerization process iterates, DNA strands identical to the original sequencing target, but of different lengths, may be produced. If enough polymerization iterations take place for an original sequencing target of n base pairs, new copies of lengths 1 through n may be produced, each terminating with a ddNTP.

The DNA strands can be observed by radiolabeling the probe and resolving each of various lengths using electrophoresis. Alternatively, the ddNTPs for each types of base (e.g., A, C, G, and T) may be fluorescently-labeled with different dyes (colors) that emit light at different wavelengths. Thus, the A ddNTPs may have one color, the C ddNTPs may have another color, and so on. This enables the use of capillary electrophoresis to separate and detect the DNA strands based on size.

In electrophoresis, the replicated sequencing targets are placed in a conductive gel (e.g., polyacrylamide). The gel is subject to an electric field. For instance, a negatively-charged anode may be placed on one side of the gel and a positively-charged cathode may be placed on the other. Since DNA is negatively charged, the sequencing targets (i.e., the elongated strands) can be introduced to the gel near the anode, and they will migrate toward the cathode. Particularly, the shorter the sequencing target, the faster and further it will migrate. After some period of time, the sequencing targets may be arranged in order of decreasing length, with longer sequencing targets near the anode and shorter sequencing targets near the cathode. Similarly, fluorescently-labeled DNA strands by resolved and detected using capillary electrophoresis.

For fluorescently-labeled DNA strands, since the terminating nucleotide of each block is a colored ddNTP, computer imaging can be used to determine the sequence of nucleotides by scanning the colored ddNTP in each sequencing targets from those near the cathode to those near the anode. Alternatively, the colored ddNTP incorporated into each block can be identified as each block migrates past a fixed detector based on its size. By reading the ordered fluorescent molecules, the computer can provide a sequence of nucleotides represented as strings of bases in letter form (e.g., ACATGCATA).

The techniques described herein, however, are not limited by the type of sequencing. To that point, advances in computer processing and storage technologies have led to so-called "next-generation sequencing" techniques. While next-generation sequencing may include various procedures, in general they involve use of massively parallel computing to speed the sequencing process. For example, rather than processing sequenced DNA block one at a time, millions of such sequencing targets may be processed in parallel.

Most genetic sequencing techniques require equipment designed for laboratories, and are not portable. Portable sequencers rely on nanopore sequencing, which uses electrophoresis to transport an unknown DNA sample through a nanometer-scale pore. A constant electric field is applied across the nanopore surface, generating a current. The electric current will vary, characteristically, depending on the nucleotide composition of the unknown sample in the pore (e.g., A, T, C or G). By monitoring the electric current as the sample passes through the pore, a computer can provide a sequence of nucleotides represented as strings of bases in letter form.

Example Data Encoding

Figure 3:
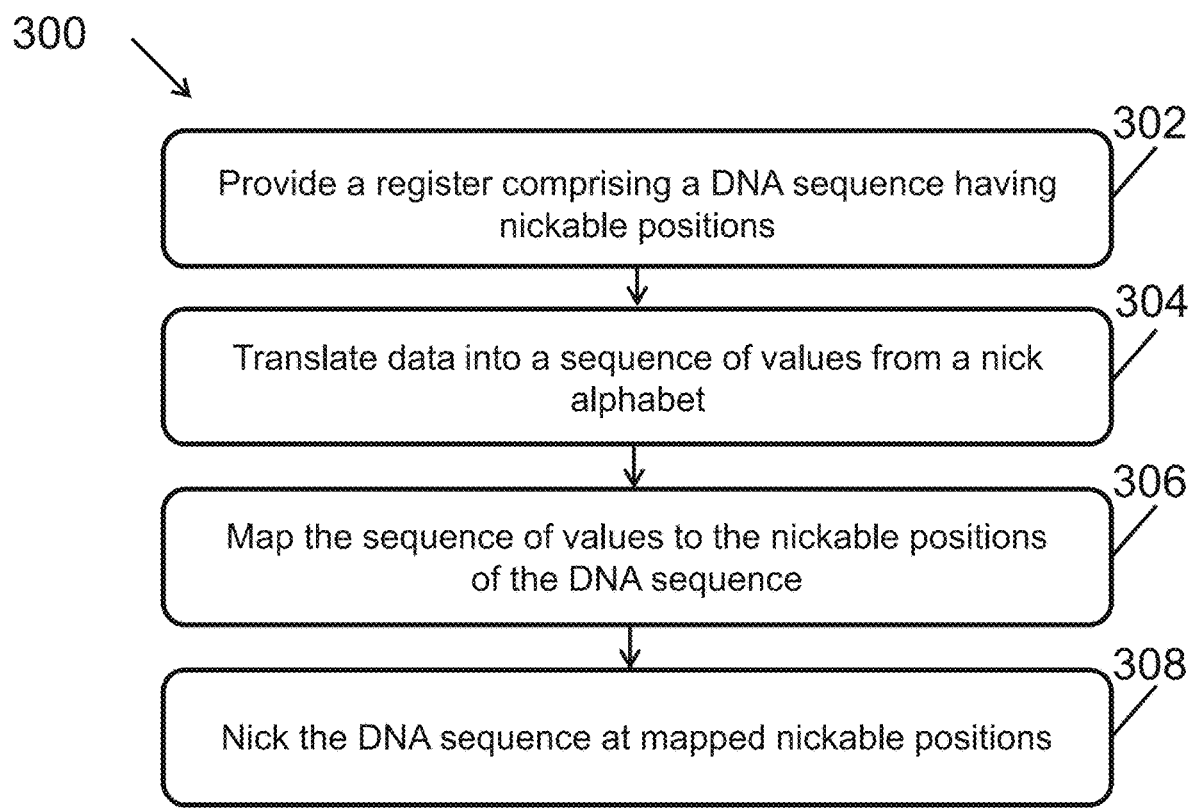
FIG. 3 depicts a flow chart illustrating a method, according to example embodiments.

During a data storage process, various embodiments may include encoding data to a register of at least one copy of a double-stranded DNA sequence having a plurality of nickable positions. As used herein, the term "register," also referred to as a "pool," can include one or more copies of a single DNA sequence, or, in certain embodiments, one or more copies of each of a plurality of distinct DNA sequences (i.e., each having a plurality of nickable positions). As used herein, the term "DNA sequence" may be used interchangeably with "DNA block" and "DNA strand." A DNA sequence may generally refer to a native DNA sequence. In alternative examples, a synthetic DNA sequence (e.g., a conventionally encoded synthetic DNA sequence) may be nicked according to the methods described herein, for instance, to provide a second layer of encoded information such as a watermark or otherwise "hidden" data. A nickable position of a DNA sequence can be described relative to the other positions of the sequence (e.g., the first, second, third, etc., nickable position of a DNA sequence), or with respect to the number of nucleotides separating a nickable position from an end of the DNA sequence (i.e., a base-pair (bp) position). An example method 300 of performing the data encoding is illustrated in FIG. 3.

At block 302, the method 300 includes providing a register comprising a double-stranded DNA sequence having a plurality of nickable positions. In certain embodiments, the register comprises a plurality of copies of the DNA sequence. For example, in certain such embodiments, the register comprises a number of copies of the DNA sequence on the order of 10, or $10^2$, or $10^3$, $10^4$, or $10^5$.

At block 304, the method 300 includes translating the data into a sequence of values from a nick alphabet including at least a first value indicating not to nick the DNA sequence, and a second value indicating to nick the DNA sequence. In certain embodiments as otherwise described herein, the second value of the nick alphabet indicates to nick a first strand of the DNA sequence. In certain such embodiments, the nick alphabet further includes a third value indicating to nick a second strand of the DNA sequence. Allowing for nicking either strand may advantageously increase the amount of data that can be stored in a given DNA sequence.

At block 306, the method 300 includes mapping the sequence of values to the plurality of nickable positions of the DNA sequence.

At block 308, the method 300 includes nicking one strand of the DNA sequence at each nickable position having a mapped value that indicates to nick the DNA sequence, in order to provide an encoded register. For example, in certain embodiments, the method 300 includes at block 308 nicking a first strand of the DNA sequence at each nickable position mapped to a value of the nick alphabet (e.g., a second value) indicating to nick the DNA sequence. In another example, in certain embodiments, the method 300 includes at block 308 nicking a first strand of the DNA sequence at each nickable position mapped to a value of the nick alphabet (e.g., a second value) indicating to nick the first strand, and nicking a second strand of the DNA sequence at each nickable position mapped to a value of the nick alphabet (e.g., a third value) indicating to nick the second strand.

One or more steps of method 300, including translating (e.g., block 304) or mapping (e.g., block 306), may be carried out by a computing device, such as computing device 200. However, the steps can be carried out by other types of devices or device subsystems. For example, translating or mapping steps of the method 300 could be carried out by a portable computer, such as a laptop or a tablet device. Any such computing device may communicate with or control a system component that stores and interacts with DNA-based registers.

Data Translation and Sequence Mapping

Figure 4:
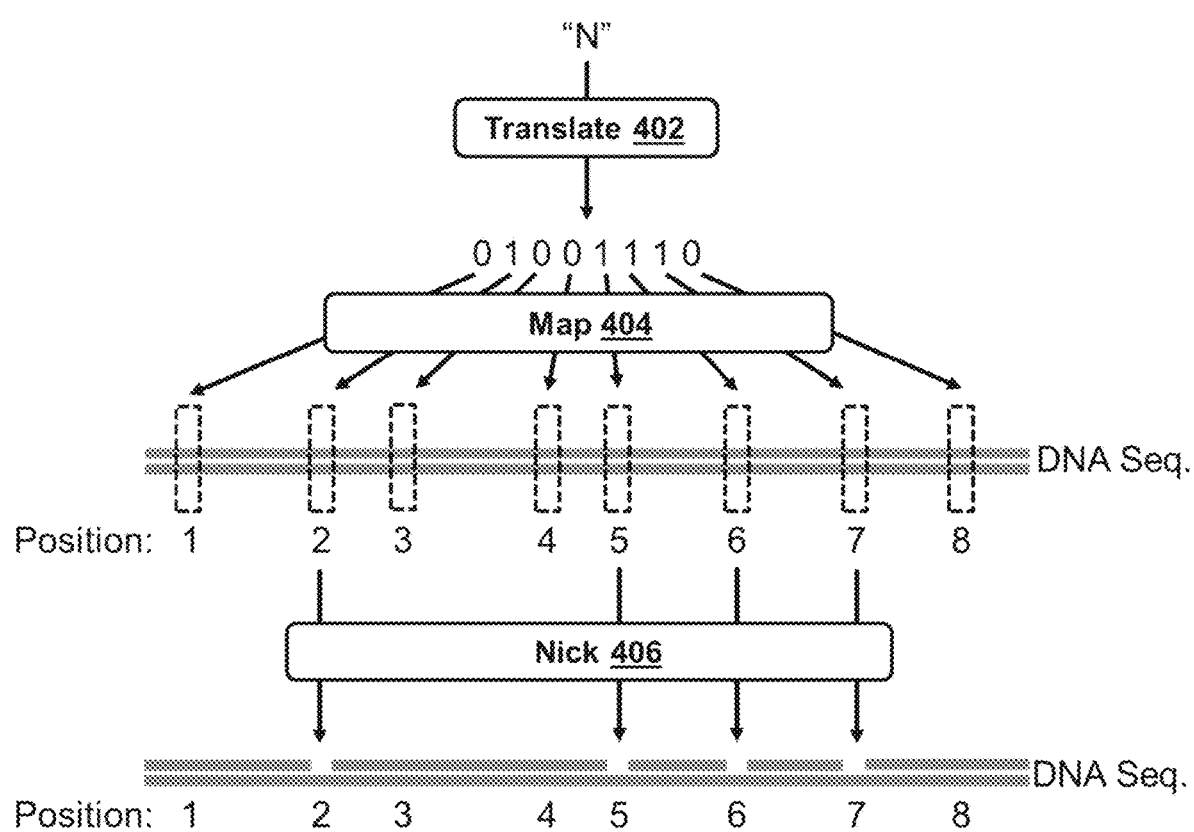
FIG. 4 illustrates a method of encoding data, according to example embodiments.

In various aspects and embodiments, data to be encoded is translated into a sequence of values from a nick alphabet. FIG. 4 is an illustration of an encoding process in accordance with an example embodiment. In FIG. 4, text to be encoded ("N") is translated into a sequence from a nick alphabet including a first value "0" and a second value "1" at block 402. In this example, the nick alphabet is a binary code, and accordingly conventional binary encoding methods can be used to translate data (e.g., ASCII text) into a sequence of nick alphabet values (e.g., "0" and "1"). As illustrated in the example embodiment of FIG. 4, the first nick alphabet value indicates not to nick the DNA sequence, and the second value indicates to nick the DNA sequence. Each nick alphabet value is mapped to a nickable position of a DNA sequence at block 404. Subsequently, each nickable position of the DNA sequence mapped to the second value of the nick alphabet is nicked at block 406. In this example, the sequence of values of the nick alphabet is 01001110, and therefore the second, fifth, sixth, and seventh nickable positions of the DNA sequence are nicked.

In certain embodiments as otherwise described herein, the second value of the nick alphabet indicates to nick a first strand of the double-stranded DNA sequence. In certain such embodiments, the nick alphabet can include a third value indicating to nick a second strand of the DNA sequence. Advantageously, a nick alphabet having a first, second, and third value (i.e., a ternary representation) facilitates higher data storage density within a register.

Figure 5A:
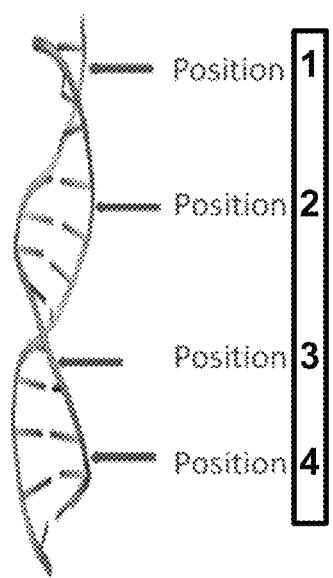
FIG. 5A illustrates a DNA sequence having nickable positions, according to example embodiments.
Figure 5B:
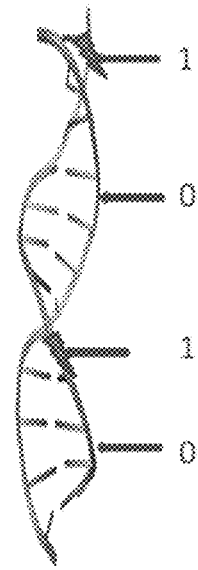
FIG. 5B illustrates an encoding scheme, according to example embodiments.
Figure 5C:
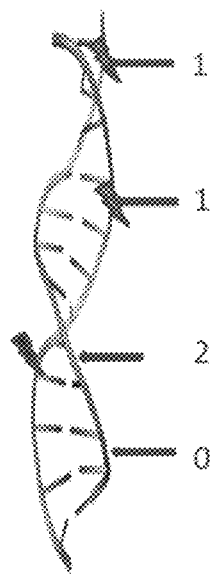
FIG. 5C illustrates an encoding scheme, according to example embodiments.

Following translation, the sequence of nick-alphabet values is mapped to the plurality of nickable positions of a register DNA sequence. The example embodiments of FIG. 5 illustrate mapping, or positionally encoding, sequences of nick alphabet values to a plurality of four nickable positions of a DNA sequence. FIG. 5A illustrates four predetermined nickable positions of a register DNA sequence. In one example, FIG. 5B illustrates mapping a sequence of values from a nick alphabet including a first value ("0") indicating not to nick the DNA sequence and a second value ("1") indicating to nick the DNA sequence. In another example, FIG. 5C illustrates mapping a sequence of values from a nick alphabet, including a first value ("0") indicating not to nick the DNA sequence, a second value ("1") indicating to nick a first strand of the DNA sequence, and a third value ("2") indicating to nick a second strand of the DNA sequence.

NA Sequence Nicking

In various aspects and embodiments, the DNA sequence is nicked at each nickable position having a mapped value that indicates to nick the DNA sequence. For example, in the example embodiment of FIG. 4, the DNA sequence is nicked at each nickable position mapped to a second value ("1") of a nick alphabet. "Nicking" refers to cleaving one strand of a double-stranded DNA sequence, e.g., by separating two previously bonded nucleotides of the strand. In certain embodiments as otherwise described herein, nicking is performed with an NA-programmable endonuclease, also referred to herein as a "nicking enzyme." For example, in certain embodiments as otherwise described herein, nicking one strand of the DNA sequence comprises cleaving the strand with a DNA-programmable endonuclease. In alternative examples, the endonuclease is RNA-programmable. In various aspects and embodiments, an NA-programmable endonuclease can be used in combination with a single-stranded guide sequence to direct strand cleavage at a particular nickable position of a DNA sequence.

Figure 6:
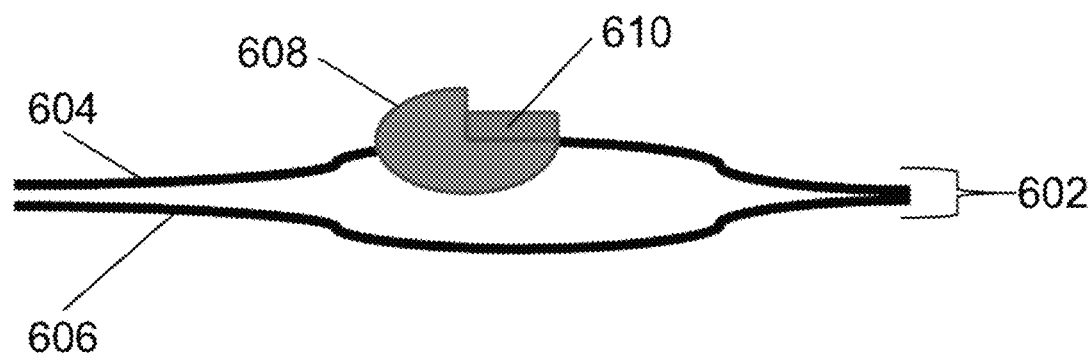
FIG. 6 illustrates a method of nicking a DNA sequence, according to example embodiments.

FIG. 6 is an illustration of a nicking step in accordance with an example embodiment. In FIG. 6, DNA sequence 602 comprises a first strand 604 and a second strand 606. In this example, nicking enzyme 608 forms a complex with strand 604 and single-stranded guide sequence 610, at a position of the DNA sequence 602 having a nucleotide subsequence complementary (or partially complementary) to guide sequence 610.

In certain embodiments as otherwise described herein, each nickable position of a DNA sequence is individually associated with a nucleotide subsequence that is unique within the DNA sequence. The length of the subsequence can be dependent on the DNA sequence. In certain desirable embodiments, DNA sequences allow for very short guides, e.g., beyond some small threshold t, all subsequences of the DNA sequence of length t are unique. In certain embodiments, this can allow for single-stranded guide sequences (e.g., for an NA-programmable endonuclease) to be of length t (and the smaller the t, the smaller the cost of the system). Furthermore, such a selection can allow for simple random access by selecting one of the unique sequences as an address sequence, as they are, by definition, avoided elsewhere in the string. For example, the genome of *E. coli* has a unique substring length of t=18 (accordingly, most fragments of the *E. coli* genome will have a unique substring length of t<18, e.g., t=17, t=16, t=15, t=14, etc.). Bacterial genomes usually have small threshold values t, but also short genome lengths. Additionally, in certain desirable embodiments, the DNA sequence does not include reverse complement repeats, which may cause undesirable nicking of both strands of a double-stranded DNA sequence.

In certain embodiments as otherwise described herein, each unique subsequence comprises at least 12 nucleotides. For example, in certain such embodiments, each unique subsequence comprises at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides. In certain embodiments as otherwise described herein, about 10% to about 70% of each unique subsequence is guanine or cytosine. For example, in certain embodiments as otherwise described herein, about 15% to about 65%, or about 20% to about 60%, or about 25% to about 55%, or about 30% to about 50% of each unique subsequence is guanine or cytosine.

In certain embodiments as otherwise described herein, any pair of nickable positions are separated in the DNA sequence by at least 16 nucleotides. For example, in certain such embodiments, any pair of nickable positions are separated in the DNA sequence by at least about 17, or at least about 18, or at least about 19, or at least about 20, or at least about 21, or at least about 22, or at least about 23, or at least about 24 nucleotides. In certain embodiments as otherwise described herein, any pair of nickable positions are separated in the DNA sequence by at least 50 nucleotides, at least 75 nucleotides, or at least 100 nucleotides.

In certain embodiments as otherwise described herein, nicking of two or more nickable positions is performed in parallel. For example, in certain such embodiments, nicking of a first and a second nickable position of a DNA sequence comprises, in parallel, cleaving a first or second strand of the DNA sequence with an NA-programmable endonuclease selective for a unique nucleotide subsequence associated with the first nickable position and cleaving a first or second strand of the DNA sequence with an NA-programmable endonuclease selective for a unique nucleotide subsequence associated with the second nickable position (e.g., separated from the first nickable position by at least 16 nucleotides). In certain embodiments as otherwise described herein, the NA-programmable endonuclease is a DNA-programmable endonuclease, such as, for example, a prokaryotic Argonaute (Ago) protein. In other embodiments, the NA-programmable endonuclease is an RNA-programmable endonuclease such as, for example, a CRISPR-associated 9 (Cas9) protein.

Ago Proteins

In various aspects and embodiments, nicking one strand of a DNA sequence at a nickable position having a mapped value that indicates to nick the DNA sequence involves providing to the register a nicking enzyme (e.g., an RNA- or DNA-programmable endonuclease) selective for the unique nucleotide subsequence associated with the mapped nickable position. In certain embodiments as otherwise described herein, the DNA-programmable endonuclease is an Ago protein, e.g., a *Pyrococcus furiosus* Ago protein ("PfAgo"). In certain such embodiments, a PfAgo protein can be used in combination with a single-stranded guide sequence corresponding (e.g., complementary, or partially complementary) to the unique nucleotide subsequence associated with the nickable position. The PfAgo protein is a DNA-guided nuclease (771 amino acids; SEQ ID NO:1) that targets cognate DNA and is most active at a temperature range from 87 to 99.9° C. It utilizes small 5'-phosphorylated DNA guides or non-phosphorylated DNA guides to cleave single-stranded DNA targets, and does not utilize RNA as a guide or a target.

Prokaryotic Argonaute (Ago) proteins from *Pyrococcus furiosus*, *Thermococcus thioreducens* (NCBI RefSeq WP_055429304), *Thermococcus onnurineus* (WP_012572468), *Thermococcus eurythermalis* (WP_050002102), *Methanocaldococcus bathoardescens* (WP_048201370), *Methanocaldococcus* sp. FS406-22 (WP_012979970), *Methanocaldococcus fervens* (WP_015791216), *Methanocaldococcus jannaschii* (WP_010870838), *Methanotorris formiscicus* (WP_052322764), *Ferroglobus placidus* (WP_012966655), *Thermogladius cellulolyticus* (WP_048163021), *Marinobacter* sp., *Thermus filiformis* (WP_038066338), *Thermus thermophilus* (WP_011229221), *Thermus* sp. NMX2.A1 (WP_038030409), *Thermus* sp. 2.9 (WP_039457454), *Thermus* sp. CCB_US3_UF1 (WP_014514637), *Thermus scotoductus* (WP_038044516), *Thermus arciformis* (SDF04754), *Thermus scotoductus*, *Thermosynechococcus* sp. NK55a (WP_041429921), *Thermosynechococcus elongates* (WP_011056792), *Thermus aquaticus*, and *Thermus parvatiensis* (WP_008631444) can be used in the methods described herein.

In certain embodiments as otherwise described herein, the Ago protein has at least 25%, or at least 30%, or at least 40%, or at least 50%, or at least 60%, or at least 70%, or at least 80%, or at least 90%, or at least 95%, or at least 99% sequence identity to a *Pyrococcus furiosus* Ago protein. In certain embodiments as otherwise described herein, the Ago protein is from thermophilic or hyperthermic bacteria or archaea. Thermophilic bacteria or archaea have growth temperatures of about 40° C. to about 75° C. or more, and an optimal growth temperature of about 60° C. Hyperthermic bacteria or archaea have growth temperatures of about 65° C. to 120° C., and an optimal growth temperature of about 80° C.

In certain embodiments as otherwise described herein, the Ago protein (e.g., PfAgo) can be present as a fusion protein and can comprise one or more additional heterologous functional domains (e.g. about or more than about 1, 2, 3, 4, 5, 6, 7, 8, 9, 10, or more domains in addition to Ago). An Ago fusion protein can comprise any additional protein sequence, and optionally a linker sequence between additional protein sequences. Examples of proteins that can be fused to Ago include, for example, tags or labels, reporter gene sequences, and proteins having one or more of the following activities: methylase activity, demethylase activity, transcription activation activity, transcription repression activity, transcription release factor activity, histone modification activity, RNA cleavage activity, nucleic acid binding activity, and helicase activity.

Examples of tags or labels include histidine (His) tags, V5 tags, FLAG tags, influenza hemagglutinin (HA) tags, Myc tags, VSV-G tags, and thioredoxin (Trx) tags. Examples of reporter genes include glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). Ago can be fused to an amino acid sequence encoding a protein or a fragment of a protein that bind DNA molecules or that bind to other cellular molecules, such as maltose binding protein (MBP), S-tag, Lex A DNA binding domain (DBD) fusions, GAL4 DNA binding domain fusions, and herpes simplex virus (HSV) BP16 protein fusions.

In certain embodiments as otherwise described herein, the unique nucleotide subsequences of a double-stranded DNA sequence comprising DNA are respective "DNA guide target sequences," i.e., subsequences within a DNA sequence to which a DNA guide sequence is designed to have complementarity, where hybridization between a DNA guide target sequence of a DNA sequence and a DNA guide sequence/Ago complex promotes the formation of an Ago complex (e.g., a complex of one or more DNA guides, one or more Ago proteins, and a DNA sequence). Full complementarity between a DNA guide molecule and a DNA guide target sequence is not necessarily required, provided there is sufficient complementarity to cause hybridization and promote formation of an Ago complex.

Typically, in the context of an Ago system, formation of an Ago complex results in cleavage of one DNA strand of the DNA sequence at a specific position within the DNA guide target sequence (i.e., within the unique subsequence associated with a nickable position).

Mixed Registers

In certain embodiments as otherwise described herein, data is encoded to a register of at least one copy of each of a plurality of distinct double-stranded DNA sequences, each having a plurality of respective nickable positions.

For example, in certain such embodiments, mapping a sequence of values from a nick alphabet comprises mapping a first portion of the sequence of values to the plurality of respective nickable positions of a first distinct DNA sequence, and mapping a second portion of the sequence of values to the plurality of respective nickable positions of a second distinct DNA sequence. In such embodiments, the method includes nicking one strand of the first DNA sequence at each respective nickable position having a mapped value that indicates to nick the DNA sequence, and nicking one strand of the second DNA sequence at each respective nickable position having a mapped value that indicates to nick the DNA sequence. In certain such embodiments, nicking of two or more nickable positions of one distinct DNA sequence is performed in parallel. In certain such embodiments, nicking of one or more nickable positions of each of two or more distinct DNA sequences is performed in parallel. Advantageously, the effective data storage capacity of registers of at least one copy of each of a plurality of distinct DNA sequences is limited only by the number of distinct DNA sequences available, and by the number of unique nucleotide subsequences (i.e., associated with respective nickable positions) for which a nicking enzyme (e.g., an NA-programmable endonuclease) is selective.

Native DNA Sequences

As noted above, advantageously, the DNA sequence of the methods as otherwise described herein can be a non-synthetic sequence, such as, for example, a nucleotide sequence native to a plant cell, a mammalian cell, an insect cell, a fungal cell, or a bacterial cell. As used herein, the term "native" and "genomic" can be used interchangeably, and both refer to DNA sequences originating in whole or in part from a plant cell, a mammalian cell, an insect cell, a fungal cell, or a bacterial cell. For example, in certain embodiments, a native DNA sequence is isolated from a cell culture, e.g., an E. coli cell culture. In other embodiments, a native DNA sequence is first isolated from a cell culture, then amplified (e.g., using PCR). In other embodiments, a native DNA sequence is first isolated from a cell culture, then modified, e.g., with a marker or tag. For example, in certain embodiments as otherwise described herein, the DNA sequence has at least 50%, or at least 60%, or at least 70%, or at least 80%, or at least 85%, or at least 90%, or at least 95%, or at least 97.5%, or at least 99% sequence identity to a nucleotide sequence native to a plant cell, a mammalian cell, an insect cell, a fungal cell, or a bacterial cell.

In certain such embodiments, the DNA sequence has at least 50%, or at least 60%, or at least 70%, or at least 80%, or at least 85%, or at least 90%, or at least 95%, or at least 97.5%, or at least 99% sequence identity to a nucleotide sequence native to an E. coli cell. For example, in certain embodiments as otherwise described herein, the DNA sequence comprises the nucleotide sequence set forth in SEQ ID NO:2. In another example, in certain embodiments as otherwise described herein, the DNA sequence comprises the nucleotide sequence set forth in SEQ ID NO:3.

As an example, using native E. coli genomes of lengths approximately $10^6$ bps (estimating that one bp occupies a volume of 1 $nm^3$), and a conservative nicking margin of 25 bps (i.e., any pair of nickable positions are separated in the DNA sequence by at least 25 nucleotides) and coding rates of 1 bit per position (or log(3) bits, accounting for possible nicking of both strands), storage densities can be of the order of $10^{18}$ bits/$mm^3$. File sizes can be potentially unlimited given the use of native DNA. Accordingly, native DNA-based storage is inherently scalable and cost efficient. Advantageously, nicking takes much less time than DNA synthesis (e.g., minutes, rather than hours or days), and writing, reading and random access require only inexpensive short synthetic primers and conventional DNA sequencing. Additionally, the short DNA guides necessary for nicking with an NA-programmable endonuclease are synthesized, but they are relatively inexpensive—the cost of synthesis increases highly nonlinearly with strand length, and the guides can have a length of for example, only 16 bps. Moreover, guide sequence can be used for many different nicking steps. Accordingly, the "per-bit" cost of the data storage described herein can be significantly less than that of conventional synthetic-DNA storage.

Advantageously, the methods as described herein are at least several orders of magnitude more cost effective compared to conventional synthetic storage, as on a strand having k nickable positions, one can effectively store k bits using a nick alphabet having two values, or k log(3) bits using a nick alphabet having three values. The cost of synthesizing primers of length ≤20 is significantly smaller than that of synthesizing long DNA strands (the cost of synthesis does not scale linearly with the length of the sequence); in addition, the unique subsequences can be used as addresses for random access. Alternatively, random access may be achieved, for example, by spatial placement of registers of a single DNA sequence (e.g., separately accessible microdots of native DNA in an ordered array). A further advantage of the methods as otherwise disclosed herein is information balancing: different information can be stored, effectively, on the two complementary strands, which is not possible with conventional symbol-based encodings that fix the content of one strand based on that of the other.

Random Access

In various aspects and embodiments, the methods as otherwise described herein can provide fully random-access storage using addressing. In the architecture, the address serves as a unique identifier for a DNA sequence that does not appear—even as a partial match of >50% similarity—anywhere in another DNA sequence of the register. Controlled access is achieved by amplifying the DNA sequence selected for reading using the address as a primer. For example, in certain embodiments as otherwise described herein, one or more unique nucleotide subsequences of a DNA sequence can serve as an address for random access.

Example Data Reading

NA Sequence Reads

Figure 7:
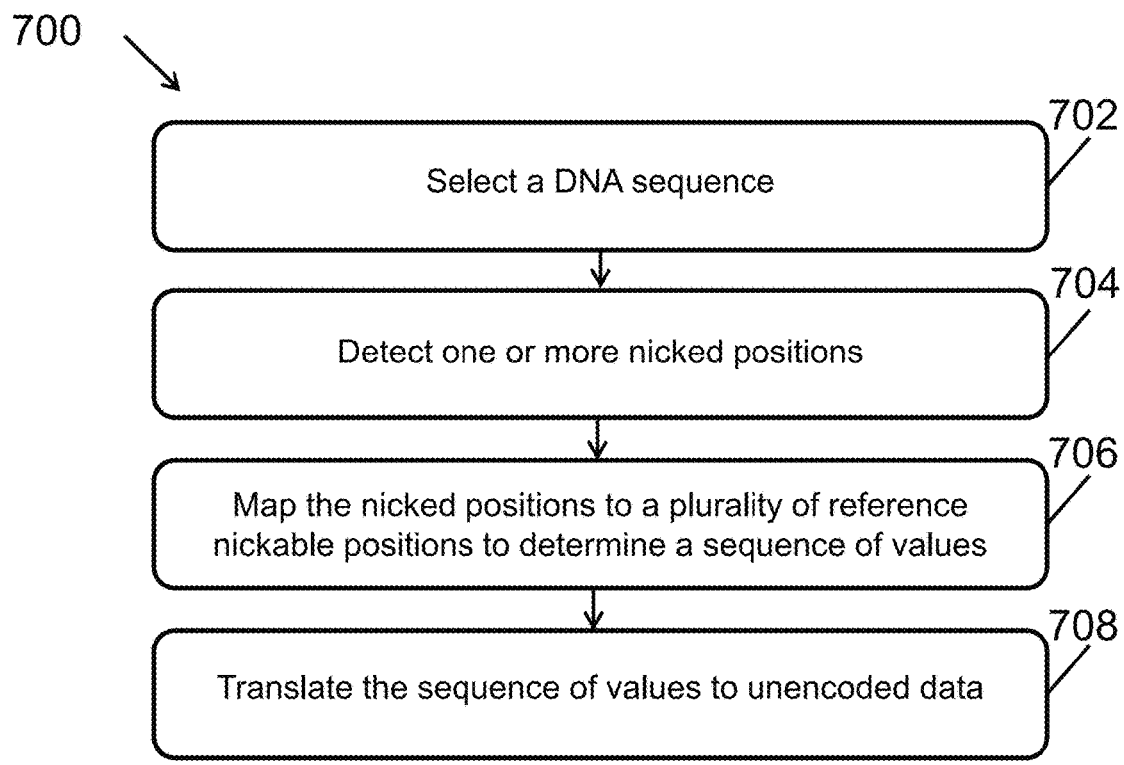
FIG. 7 depicts a flow chart illustrating a method, according to example embodiments.

The data of an encoded register as otherwise disclosed herein may later be read for data retrieval. An example method 700 of performing the random access reading is illustrated in FIG. 7.

At block 702, the method 700 includes selecting a specific DNA sequence (e.g., based on a unique nucleotide subsequence of the DNA sequence), from a register. In certain embodiments, the selection may be made using PCR to amplify the DNA sequence from a mixed register. In other embodiments, the selection may be selecting a register of one or more copies of a single DNA sequence.

At block 704, the method 700 includes detecting one or more nicked positions of the DNA sequence. This may include sequencing the DNA sequence, e.g., with a nanopore-based storage device. During the reading process, the DNA sequence being read may be selected from the register and analyzed. In doing so, that respective DNA sequence may be removed from the register and/or destroyed. As such, the reading process may include a replenishment of the read DNA sequence. The replenishment may include returning a copy of the amplified/sequences DNA sequence to the register.

In certain embodiments as otherwise described herein, detecting the one or more nicked positions of a DNA sequence comprises denaturing the selected DNA sequence to provide a plurality of nucleic acid strands, wherein each strand has a nucleotide subsequence corresponding to a portion of the DNA sequence bounded by any two of the nicked positions, a first end of the DNA sequence, and a second end of the DNA sequence. In certain embodiments, denaturing the DNA sequence includes heating the DNA sequence (e.g., maintaining the DNA sequence at about 100° C. for 5-10 minutes), then cooling the DNA sequence (e.g., to about 4° C.). In certain embodiments, denaturing the DNA sequence includes immunoprecipitating the plurality of DNA strands. The plurality of nucleic acid strands are sequenced and aligned to a reference sequence of the encoded register. In certain such embodiments, the reference sequence of the encoded register includes a plurality of reference nickable positions of a selected DNA sequence.

At block 706, the method 700 includes mapping the one or more nicked positions of the DNA sequence to a plurality of reference nickable positions of a reference sequence of the encoded register (i.e., including a plurality of reference nickable positions of a selected DNA sequence) to determine a sequence of values from a nick alphabet. In certain embodiments as otherwise described herein, the nick alphabet includes a first value indicating that the DNA sequence was not nicked at a reference nickable position and a second value indicating that the DNA sequence was nicked at a reference nickable position. In certain such embodiments, the second value indicates that a first strand of the DNA sequence was nicked at a reference nickable position, and the nick alphabet further includes a third value indicating that a second strand of the DNA sequence was nicked at a reference nickable position.

At block 708, the method 700 includes translating the sequence of values from the nick alphabet into unencoded data.

One or more steps of method 700, including aligning (e.g., block 704), mapping (e.g., block 706), or translating (e.g., block 708), may be carried out by a computing device, such as computing device 200. However, the steps can be carried out by other types of devices or device subsystems. For example, the aligning, mapping, or translating steps of the method 700 could be carried out by a portable computer, such as a laptop or a tablet device. Any such computing device may communicate with or control a system component that stores and interacts with DNA-based registers.

Figure 8:
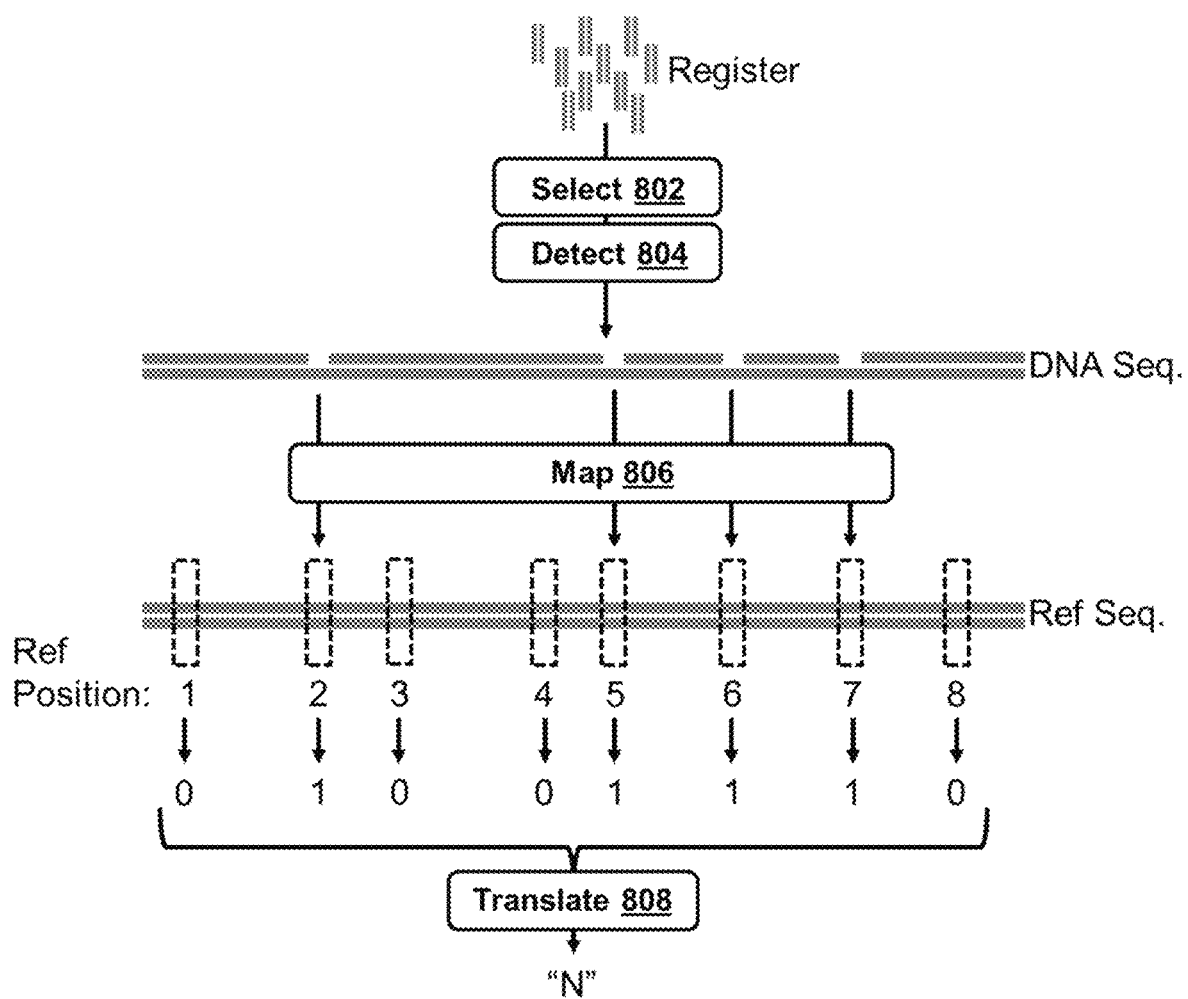
FIG. 8 illustrates a method of reading data, according to example embodiments.

FIG. 8 is an illustration of a reading process in accordance with an example embodiment. In FIG. 8, a DNA sequence from an encoded register to read is first selected at block 802. The nicked positions of the selected DNA sequence are then detected at block 804. Subsequently, the nicked positions are mapped to the reference nickable positions of a reference sequence to determine a sequence of value from a nick alphabet at block 806. The reference sequence includes each nickable position that could have been nicked during a data saving process. In the example embodiment of FIG. 8, the sequence of values includes a first value of a nick alphabet ("0") indicating that the DNA sequence was not nicked at a reference nickable position, and a second value of a nick alphabet ("1") indicating that the DNA sequence was nicked at a reference nickable position. In this example, the second, fifth, sixth, and seventh nickable positions of the DNA sequence were determined to be nicked, and therefore the resulting sequence of values of the nick alphabet is 01001110. Finally, the sequence of values is translated into unencoded data at block 808.

In one example, high-throughput sequencing (e.g., MiSeq high-throughput sequencing) with laboratory platforms may be performed. In such embodiments, the different lengths of the fragments can be addressed by performing run-length encoding in addition to positional encoding to avoid large differences in the lengths of the fragments. In another example, sequencing with portable, nanopore-based platforms may be performed. Such platforms easily accommodate longer fragments of different lengths and allow for portable structures.

Example Data Computation

Nick Displacement

Figure 9:
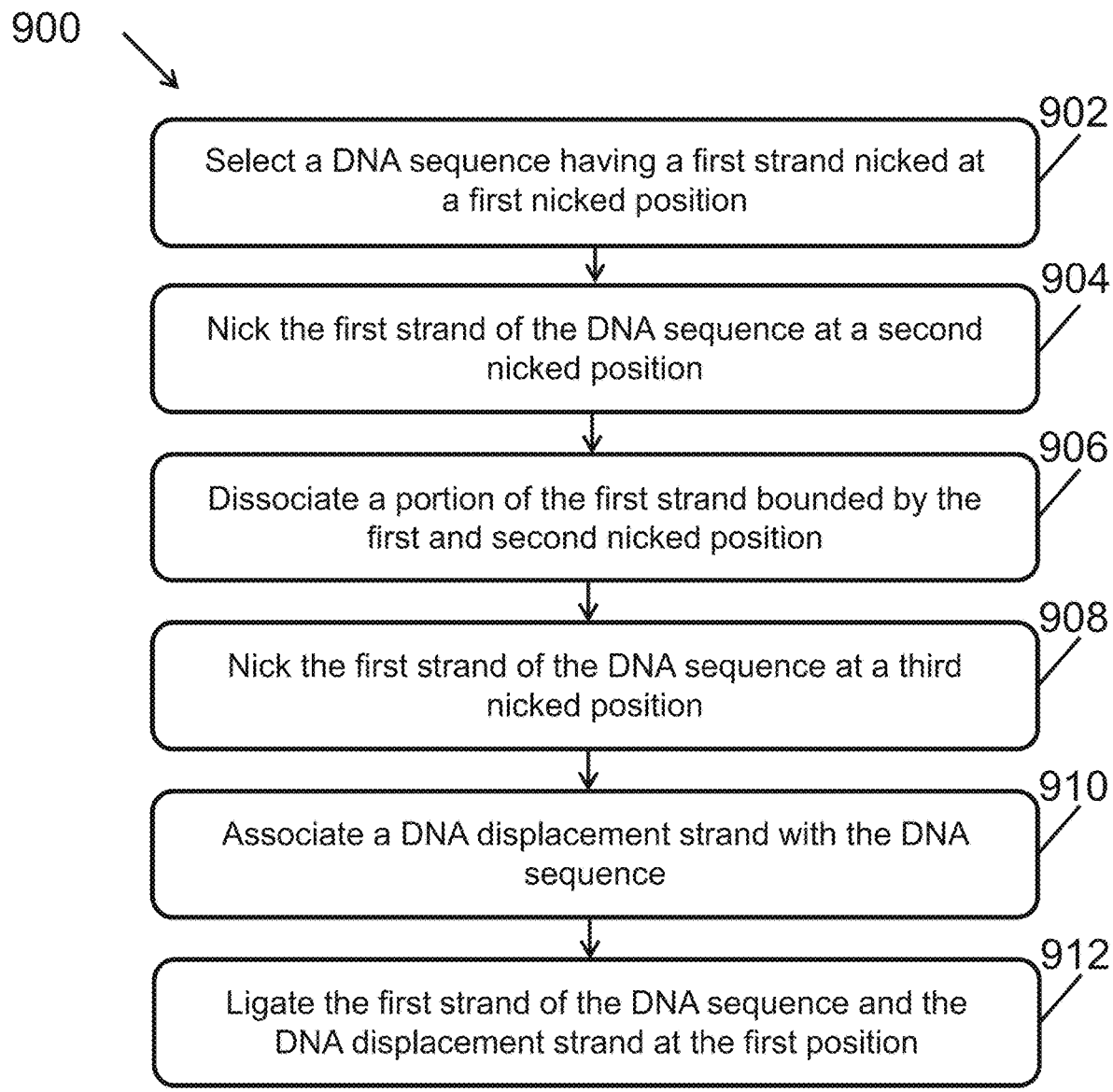
FIG. 9 depicts a flow chart illustrating a method, according to example embodiments.

Computations may be performed on an encoded register as otherwise disclosed herein. In one example, the computation includes displacement of a nicked position of a DNA sequence of an encoded register. An example method 900 of performing the nick displacement is illustrated in FIG. 9.

At block 902, the method 900 includes selecting from a register a specific DNA sequence having a first strand nicked at a first nicked position. In certain embodiments, the selection may be made using PCR to amplify the DNA sequence from a mixed register. In other embodiments, the selection may be selecting a register of one or more copies of a single DNA sequence.

At block 904, the method 900 includes nicking the first strand of the DNA sequence at a second nicked position. For example, in certain embodiments, nicking the first strand of the DNA sequence at a second nicked position includes cleaving the first strand with an RNA- or DNA-programmable endonuclease (e.g., Cas9 or PfAgo).

At block 906, the method 900 includes dissociating a portion of the first strand bounded by the first and second nicked positions. Dissociation of the bounded portion ("nick elongation") of the first strand provides a single stranded portion of the DNA sequence (i.e., a "toehold" portion of the DNA sequence). In certain embodiments as otherwise described herein, the second nicked position is separated from the first nicked position by at least 3 nucleotides, or by at least 4 nucleotides, or by at least 5 nucleotides (i.e., providing a toehold portion of the DNA sequence having a length of 3, 4, or 5 nucleotides). In certain embodiments as otherwise described herein, the second nicked position is separated from the first nicked position by at most 15 nucleotides. In certain such embodiments, the second nicked position is separated from the first nicked position by a sequence of nucleotides having a length of at least 6 nucleotides and at most 15 nucleotides, or at least 7 nucleotides and at most 14 nucleotides, or at least 8 nucleotides and at most 13 nucleotides.

At block 908, the method 900 includes nicking the first strand of the DNA sequence at a third nicked position ("nick addition") separated from the first nicked position by the second nicked position. In certain embodiments as otherwise described herein, the third nicked position is separated from the first nicked position by at least 16 nucleotides. For example, in certain such embodiments, the third nicked position is separated from the first nicked position by at least about 17, or at least about 18, or at least about 19, or at least about 20, or at least about 21, or at least about 22, or at least about 23, or at least about 24 nucleotides.

At block 910, the method 900 includes associating a DNA displacement strand with the single-stranded portion of the DNA sequence ("string migration"), and displacing from the DNA sequence a portion of the first strand bounded by the second nicked position and the third nicked position. A DNA displacement strand having a sequence sufficiently complementary to the single-stranded portion of the DNA sequence, and further sufficiently complementary to the portion of the second strand of the DNA sequence bounded by the second nicked position and the third nicked position, can be selected.

At block 912, the method 900 includes ligating the first strand of the DNA sequence and the DNA displacement strand at the first nicked position. In certain embodiments as otherwise described herein, ligating the first strand of the DNA sequence and the DNA displacement strand comprises bonding the respective nucleotides of the DNA sequence and the DNA displacement strand adjacent to the first nicked position with a DNA ligase enzyme. For example, in certain such embodiments, the DNA ligase enzyme is a T4 DNA ligase or an *E. coli* DNA ligase.

Figure 10:
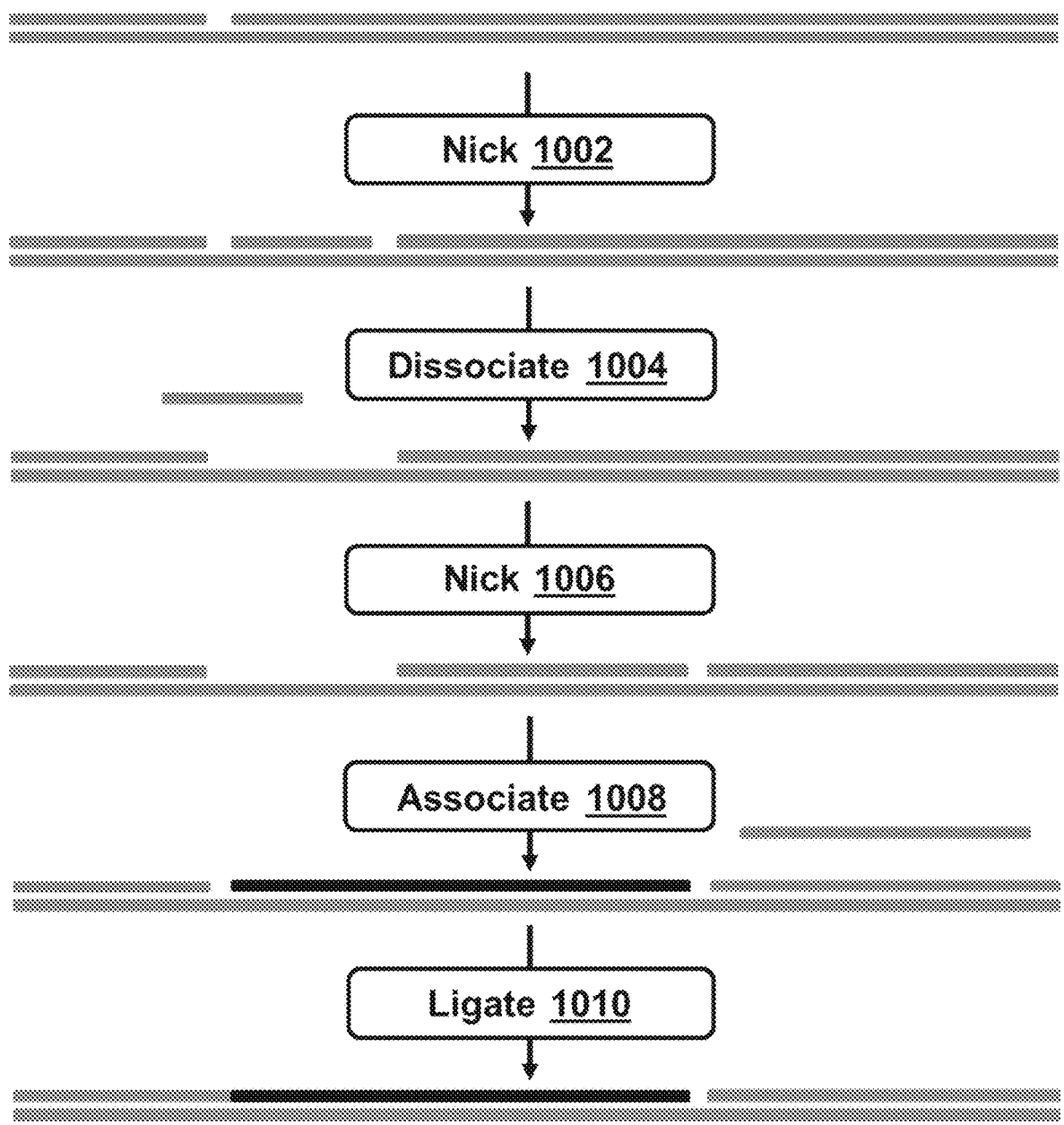
FIG. 10 illustrates a method of nick displacement, according to example embodiments.

FIG. 10 is an illustration of a nick displacement process in accordance with an example embodiment. In FIG. 10, a DNA sequence having a first nicked position on a first strand is nicked at a second nicked position on the first strand at block 1002. The portion of the first strand bounded by the first and second nicked positions is dissociated at block 1004. Subsequently, the first strand of the DNA sequence is nicked at a third nicked position at block 1006. A DNA displacement strand (i.e., complementary or partially complementary to the single-stranded portion of the DNA sequence) is associated with the DNA sequence, and the portion of the first strand of the DNA sequence bounded by the second and third nicked positions is dissociated at block 1008. Finally, the first strand of the DNA sequence and the DNA displacement sequence are ligated at the first nicked position at block 1010.

As shown in FIG. 10, if a nick is to be "moved" or displaced to another position, the double-stranded DNA sequence has to be processed at the nick position so as to elongate the cut and accommodate binding of the toehold sequence. The procedure is similar to strand displacement, but can be based entirely on non-synthetic, or native DNA. Nick displacement can be used, for example, to perform data rewriting "in-memory."

Counting and Comparison Operations

In-memory counting, comparisons and other operations can be executed via nick displacement. Counting amounts to controlled addition, while comparing encompasses thresholding. Hence, any nonlinear data processing algorithms (such as neuron-associated computations and Minsky's machines) may be implemented in-memory, thereby ensuring computational versatility. The described operations represent a powerful basis for performing learning tasks, implementing event counters, and in general, rewriting the stored information, without reading the data, and without integration with silicon logic. Because nick displacement can be performed in seconds and in a highly precise manner, using only short DNA displacement strands that also serve the dual purpose of addresses, the architecture can be highly flexible. Furthermore, as nick displacement may be performed in parallel on multiple strands of native DNA, efficient parallel implementations are possible.

Conclusion

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

EXAMPLES

The Examples that follow are illustrative of specific embodiments of the invention, and various uses thereof. They are set forth for explanatory purposes only, and are not to be taken as limiting the invention.

Example 1. Data Encoding with PfAgo

Figure 11:
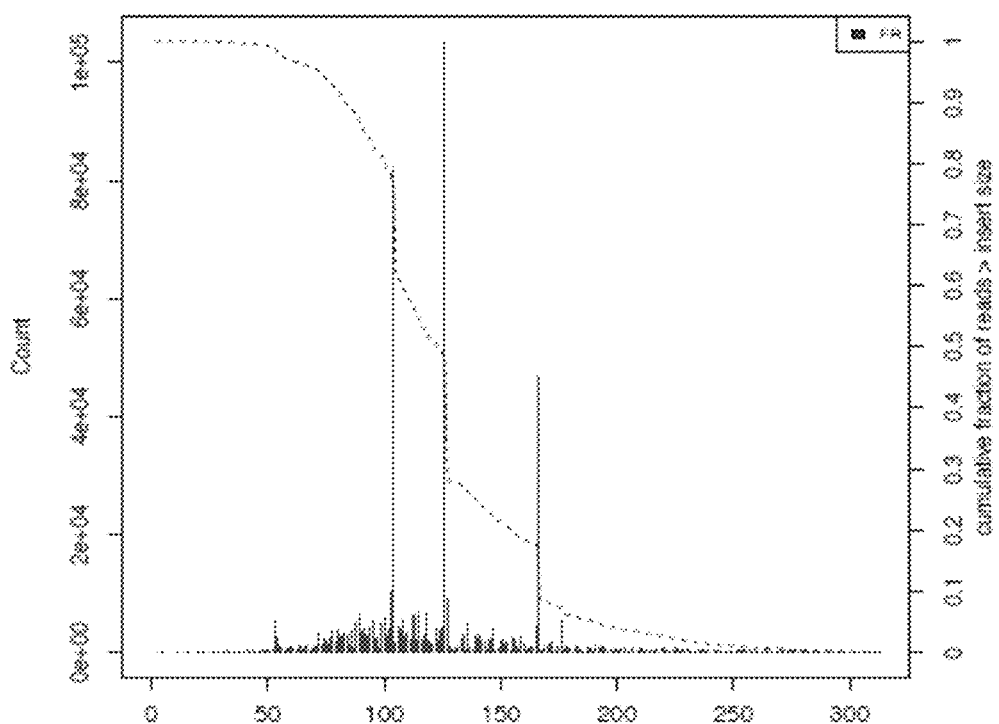
FIG. 11 depicts a graph showing the base pair (bp) length of the DNA fragments obtained by denaturing a DNA sequence of an encoded register of the Examples.
Figure 12:
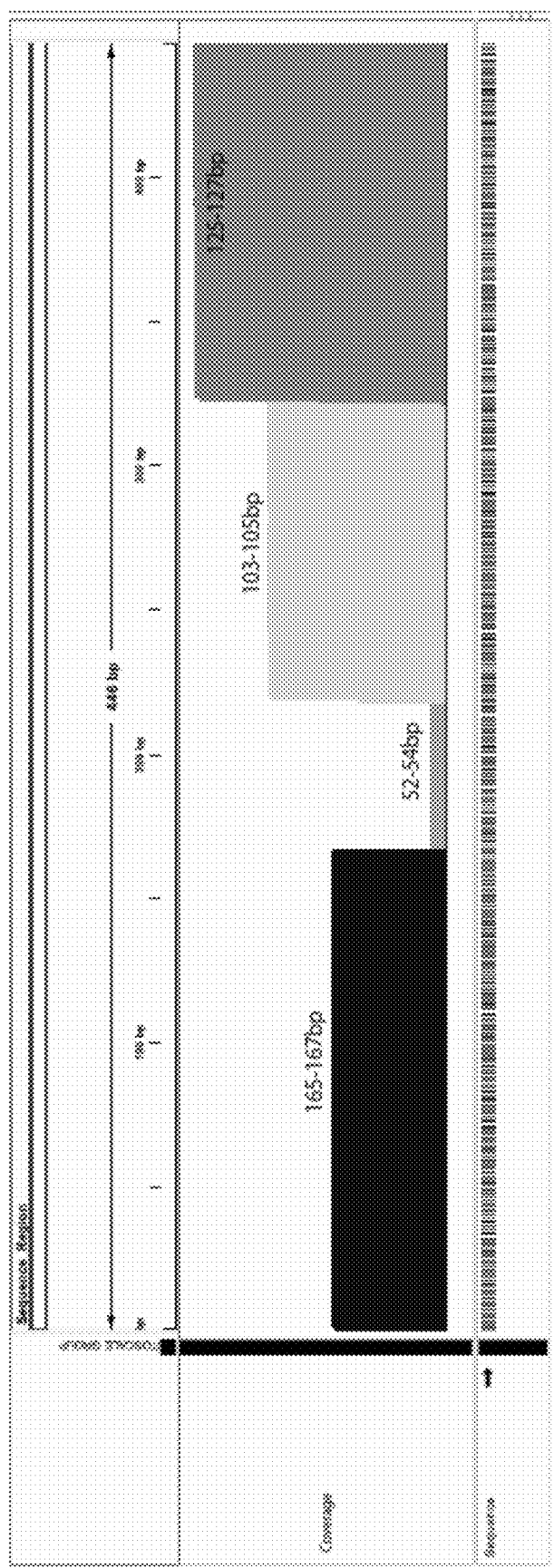
FIG. 12 depicts the alignment to a reference sequence of the DNA fragments obtained by denaturing a DNA sequence of an encoded register of the Examples.

A 449-bp DNA sequence native to E. coli (SEQ ID NO:3) was nicked at three nickable positions (166 bp, 219 bp, and 323 bp) of the same strand with PfAgo (SEQ ID NO:1). The nicked DNA sequence was then denatured into single-stranded fragments, which were sequenced and aligned to a reference sequence of the 449-bp E. coli DNA sequence. The resulting fragments and alignment, shown in FIGS. 11-12, indicated five single-stranded DNA fragments, corresponding to the non-nicked strand of the DNA sequence (449 bps), and the four strands bounded by three nicked positions and the ends of the DNA sequence (53 bps, 104 bps, 126 bps, and 166 bps). The results demonstrate that PfAgo can accurately nick one or more nickable positions of a DNA sequence to provide register-encoded data.

Example 2. Data Encoding with PfAgo

Figure 13:
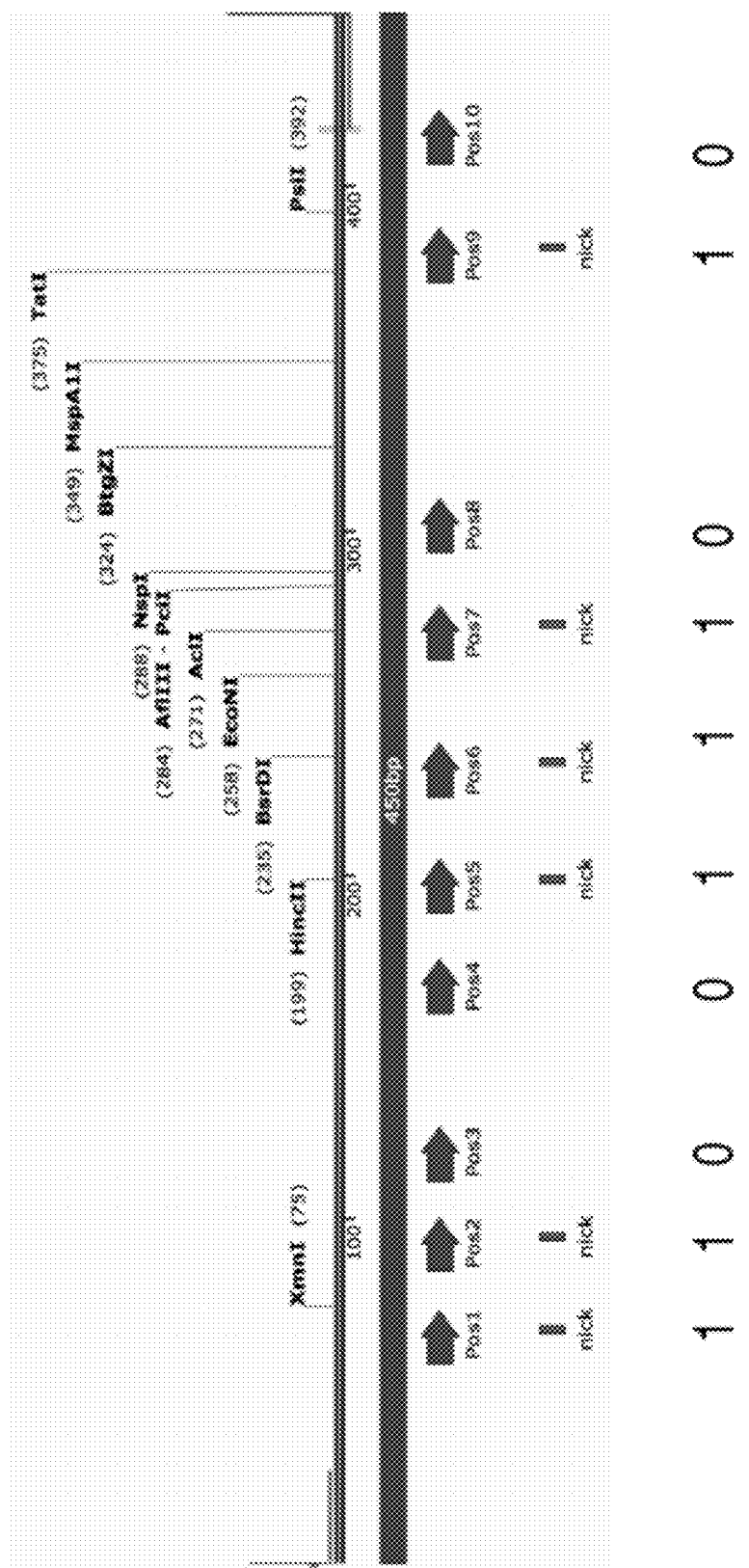
FIG. 13 depicts a sequence of values from a nick alphabet ("0" and "1") mapped to a DNA sequence having 10 nickable positions ("Pos1"-"Pos10"). The DNA sequence (SEQ ID NO:2) is native to an *E. coli* cell.
Figure 14:
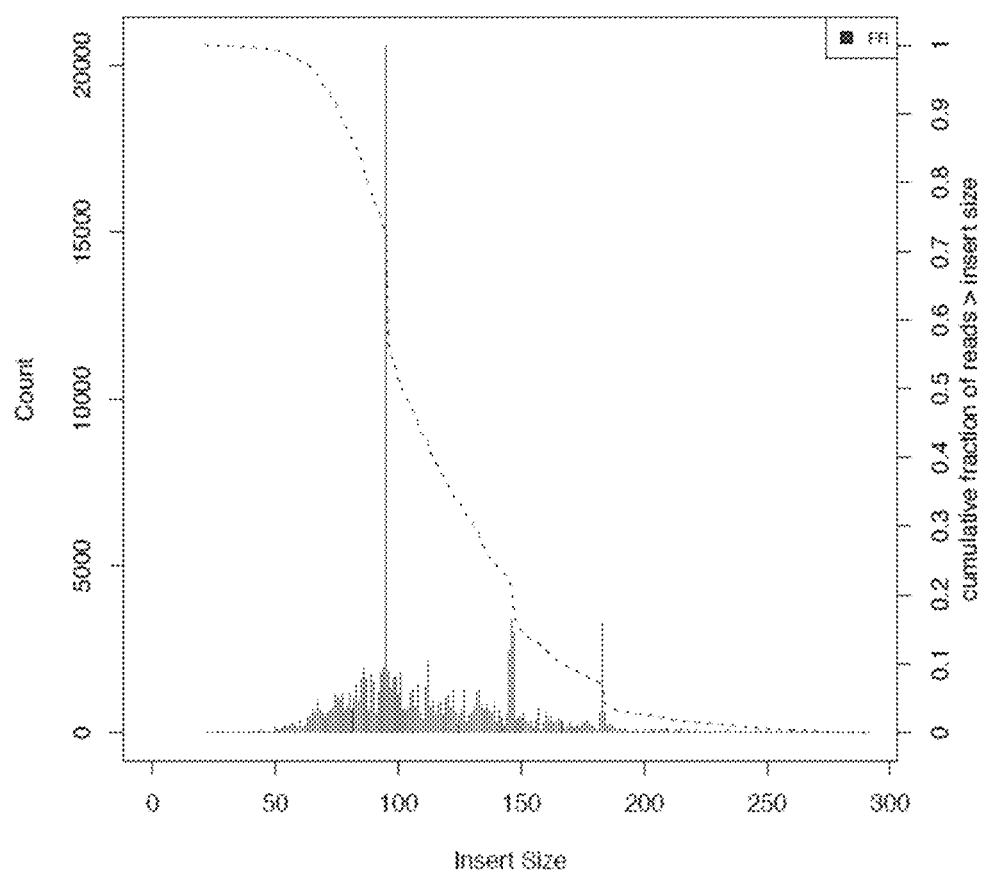
FIG. 14 depicts a graph showing the bp length of the DNA fragments obtained by denaturing a DNA sequence of an encoded register of the Examples.
Figure 15:
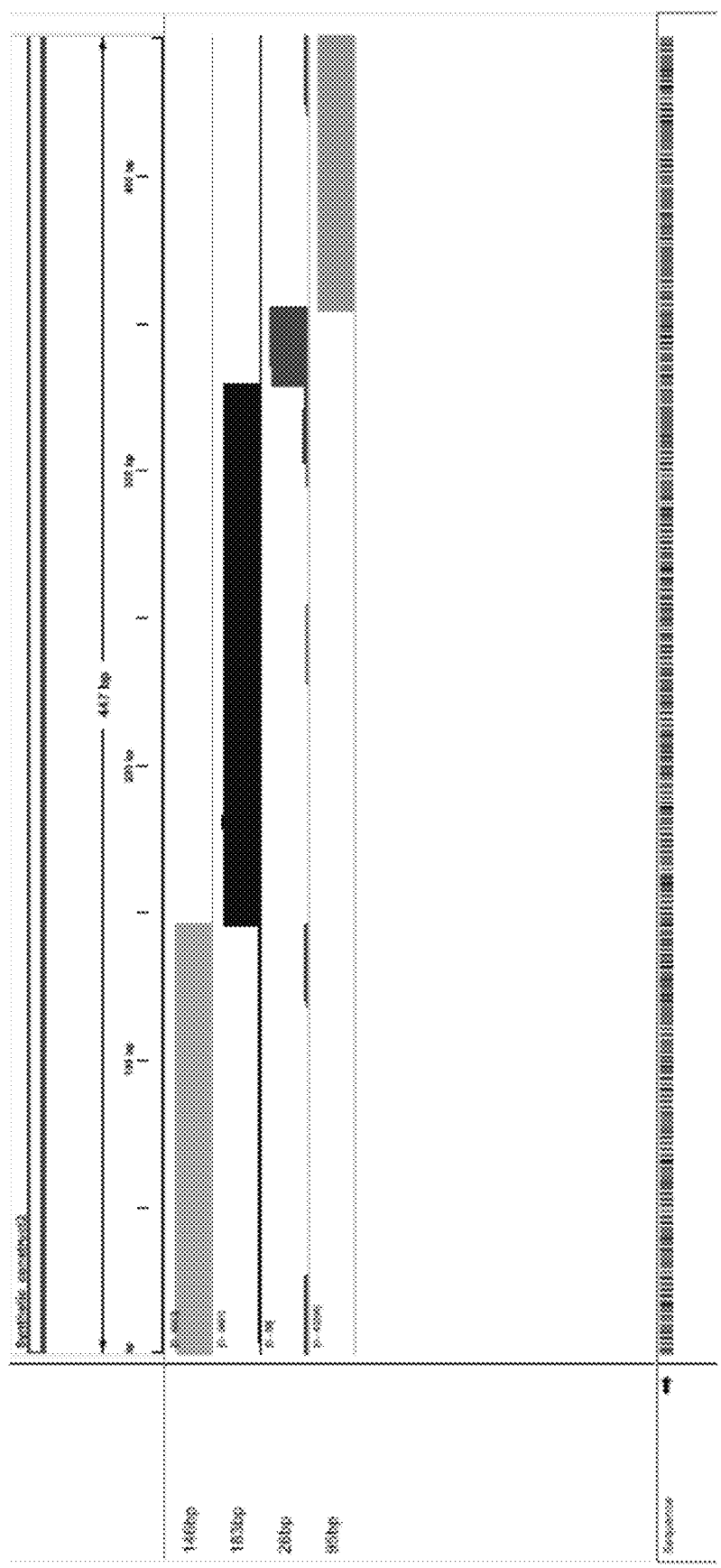
FIG. 15 depicts the alignment to a reference sequence of the DNA fragments obtained by denaturing a DNA sequence of an encoded register of the Examples.
Figure 16:
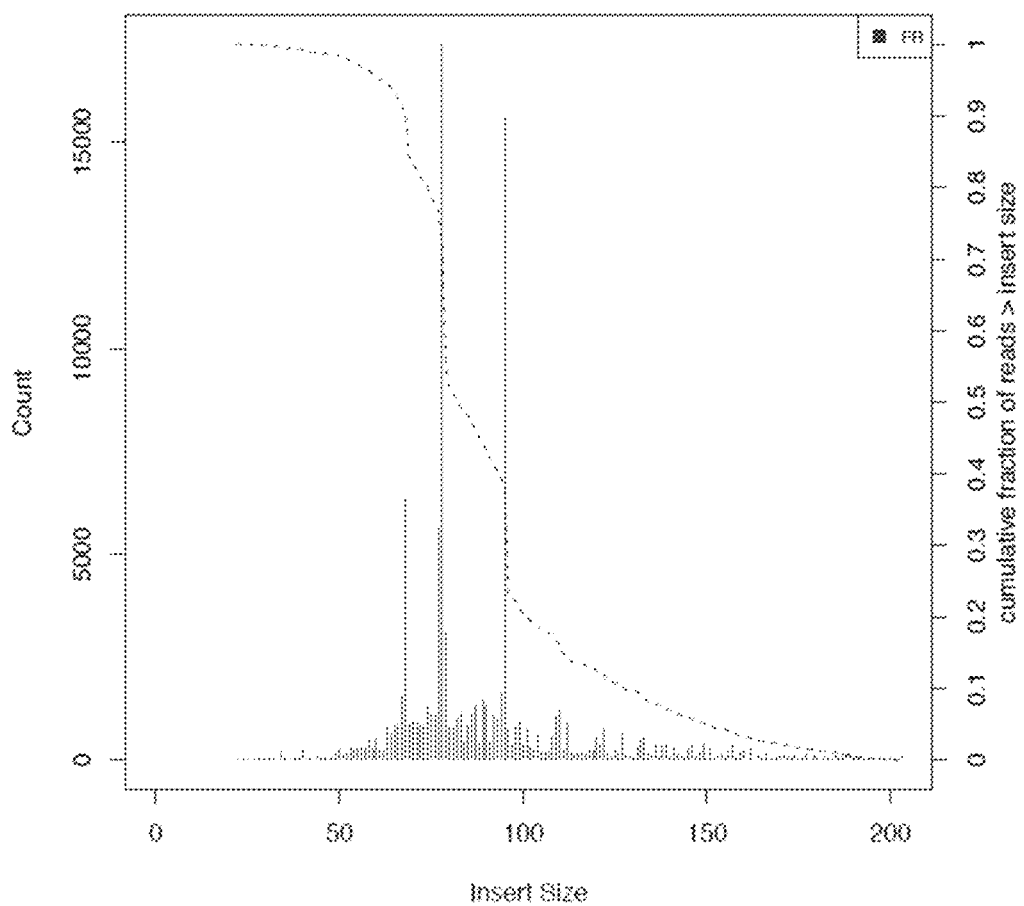
FIG. 16 depicts a graph showing the bp length of the DNA fragments obtained by denaturing a DNA sequence of an encoded register of the Examples.
Figure 17:
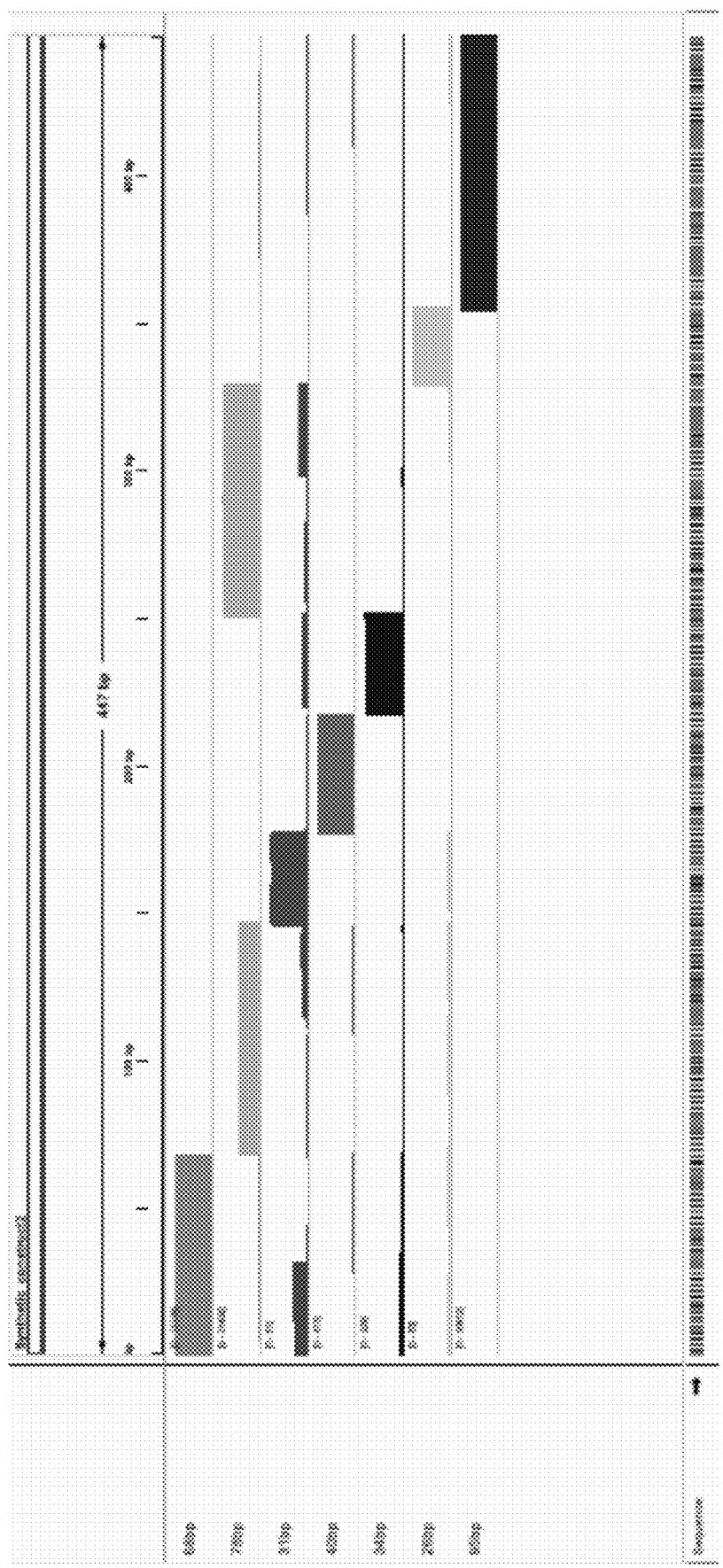
FIG. 17 depicts the alignment to a reference sequence of the DNA fragments obtained by denaturing a DNA sequence of an encoded register of the Examples.
Figure 18:
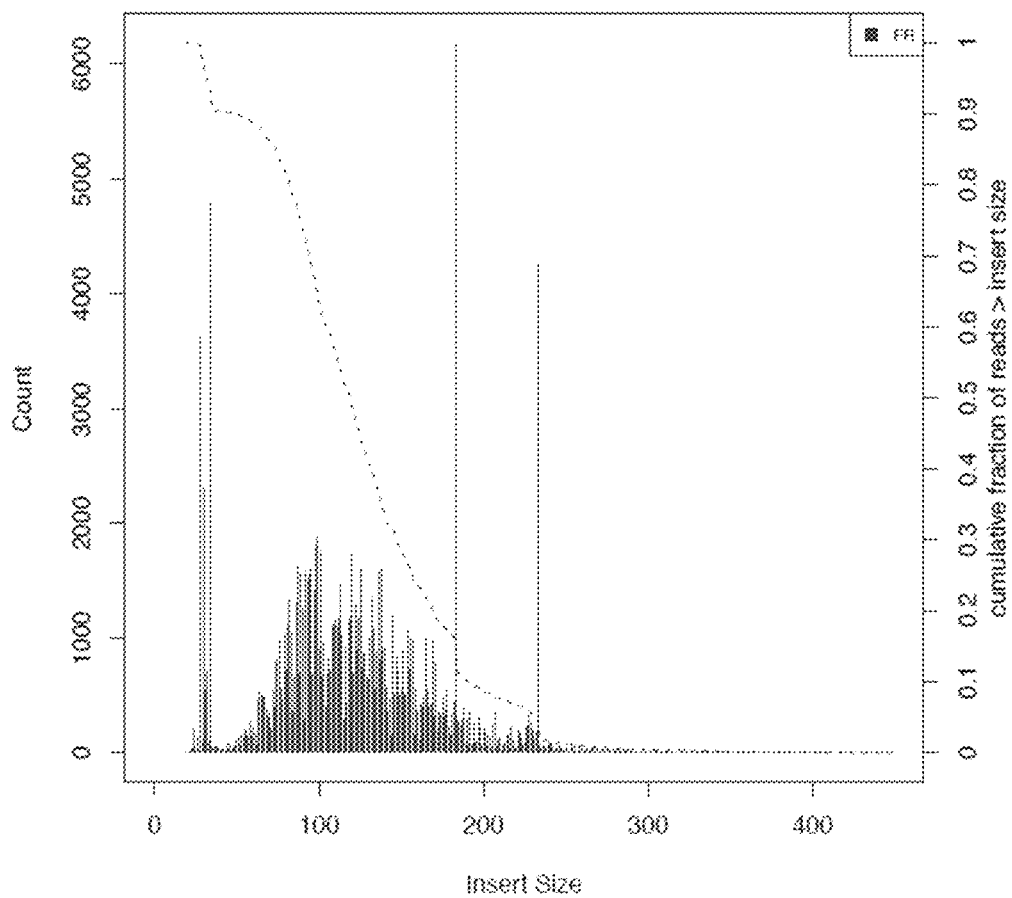
FIG. 18 depicts a graph showing the bp length of the DNA fragments obtained by denaturing a DNA sequence of an encoded register of the Examples.
Figure 19:
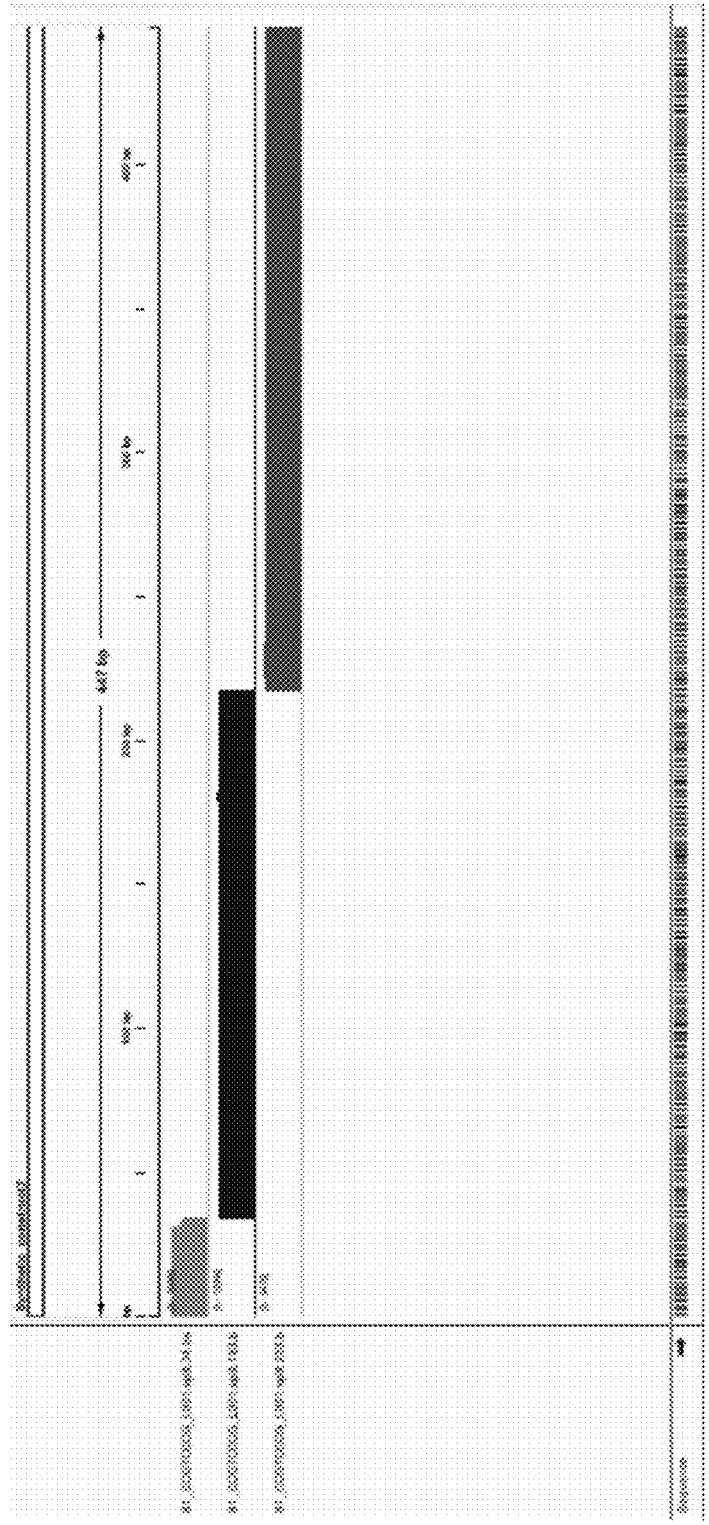
FIG. 19 depicts the alignment to a reference sequence of the DNA fragments obtained by denaturing a DNA sequence of an encoded register of the Examples.

The 272-word Gettysburg Address, in ASCII-coded text, was converted to a sequence of nick alphabet values, where "0" indicated not to nick a DNA sequence, and "1" indicated to nick the DNA sequence. The sequence of nick alphabet values was separated into 281 segments of 10 nick alphabet values, and each segment was mapped to the DNA sequence of a register of multiple copies of a 450-bp DNA sequence native to E. coli (SEQ ID NO:2), for nicking by PfAgo (SEQ ID NO:1). Encoding of a sample segment, "1100111010," is shown in FIG. 13.

Each register contained 100 ng of the 450-bp DNA sequence (0.36 pmol). 10 pmols of PfAgo was used to nick each register. In total, 100 pmol of DNA guide sequences was used for nicking. The nicking reactions were performed in 50 uL of 2× buffer containing 40 mM HEPES, 300 mM NaCl and 4 mM $MnCl_2$ at pH=7.

Three consecutive registers, corresponding to segments 79-81 of 281, were selected for verification. The nick alphabet translation mapped to each DNA sequence, as well as the lengths of single-stranded DNA fragments expected from denaturing each DNA sequence, are listed in Table 2, below.

TABLE 2

| Register Verification | | |
|---|---|---|
| Register No. (of 281) | Nick Alphabet Translation | Expected Fragment Lengths (bps) |
| 79 | 0110000100 | 26, 95, 146, 183 |
| 80 | 0110111110 | 26, 31, 34, 40, 68, 78, 78, 95 |
| 81 | 0000010001 | 34, 183, 233 |

For each selected register, the nicked DNA sequence was purified using a Qiagen PCR clean-up kit and denatured into single-stranded fragments (100° C., 5-10 min.), which were subjected to library preparation (Accel-NGS® 1S Plus DNA Library Kit), sequenced (MiSeq), and aligned to a reference sequence of the 450-bp E. coli DNA sequence. The resulting fragments and alignments, shown in FIGS. 14-15, 16-17, and 18-19 for registers 79, 80, and 81, respectively, matched the expected lengths of Table 2. The results demonstrate the outstanding data integrity of nick-based data storage in registers of non-synthetic DNA sequences.

Example 3. "Toehold" Formation for Nick Displacement

Figure 20:
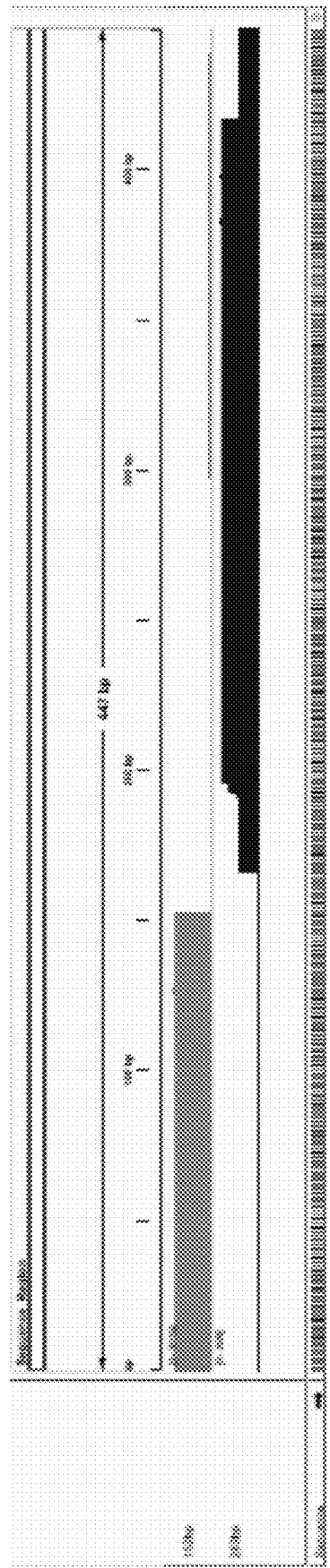
FIG. 20 depicts the alignment to a reference sequence of the DNA fragments obtained by denaturing a DNA sequence having a single-stranded portion, according to the Examples.

A 449-bp DNA sequence native to E. coli (SEQ ID NO:3), having a first strand nicked at a first position (152 bp), was nicked at a second position (166 bp) by PfAgo (SEQ ID NO:1). Following dissociation of the portion of the first strand bounded by the first and second nicked positions, the DNA sequence was sequenced. The resulting alignment (FIG. 20) is missing the 14-bp portion of the first strand, between the 152-bp and 166-bp positions. The results show successful creation of a "toehold" sequence, allowing for nick displacement (i.e., to a third nicked position).

TABLE 3

Sequences Disclosed Herein

SEQ ID NO: 1

TABLE 3-continued

Sequences Disclosed Herein

*Pyrococcus furiosus*
```
MKAKVVINLV KINKKIIPDK IYVYRLFNDP EEELQKEGYS IYRLAYENVG IVIDPENLII   60
ATTKELEYEG EFIPEGEISF SELRNDYQSK LVLRLLKENG IGEYELSKLL RKFRKPKTFG  120
DYKVIPSVEM SVIKHDEDFY LVIHIIHQIQ SMKTLWELVN KDPKELEEFL MTHKENLMLK  180
DIASPLKTVY KPCFEEYTKK PKLDHNQEIV KYWYNYHIER YWNTPEAKLE FYRKFGQVDL  240
KQPAILAKFA SKIKKNKNYK IYLLPQLVVP TYNAEQLESD VAKEILEYTK LMPEERKELL  300
ENILAEVDSD IIDKSLSEIE VEKIAQELEN KIRVRDDKGN SVPISQLNVQ KSQLLLWTNY  360
SRKYPVILPY EVPEKFRKIR EIPMFIILDS GLLADIQNFA TNEFRELVKS MYYSLAKKYN  420
SLAKKARSTN EIGLPFLDFR GKEKVITEDL NSDKGIIEVV EQVSSFMKGK ELGLAFIAAR  480
NKLSSEKFEE IKRRLFNLNV ISQVVNEDTL KNKRDKYDRN RLDLFVRHNL LFQVLSKLGV  540
KYYVLDYRFN YDYIIGIDVA PMKRSEGYIG GSAVMFDSQG YIRKIVPIKI GEQRGESVDM  600
NEFFKEMVDK FKEFNIKLDN KKILLLRDGR ITNNEEEGLK YISEMFDIEV VTMDVIKNHP  660
VRAFANMKMY FNLGGAIYLI PHKLKQAKGT PIPIKLAKKR IIKNGKVEKQ SITRQDVLDI  720
FILTRLNYGS ISADMRLPAP VHYAHKFANA IRNEWKIKEE FLAEGFLYFV            770
```
SEQ ID NO: 2

*Escherichia coli*
```
actctgaatt tttgcggtgg tttcaagaag gattttttct ttaagagaaa ctatttcttt   60
caatccatca gaaatttttc ttttaatcac aacaccattt gcaggagatt ttatcaagct  120
catctctatt ttttttcgca taaaatgtaa ttctctctaa aagtgttgat gcaagtggta  180
acggcgattg tatgtggtca acaaaatcag gaaataataa attaaatcgt tgctgcattg  240
ccaatggttg ttgccttata tagggtaaca acgttgaaaa accacatgtg atgatattgt  300
gatagttagc gatgccgggt ttgtatcgtg cctttttcatt tatttccagc ggtatagctg  360
ataaataatc ccttagtaca tcaggaacct tataaaaaaa cccgcgttct gcaaaccttt  420
ctcgataaaa gtgacaacca ctgagtaaac                                   450
```
SEQ ID NO: 3

*Escherichia coli*
```
gtgatagtta gcgatgccgg gtttgtatcg tgccttttca tttatttcca gcggtatagc   60
tgataaataa tcccttagta catcaggaac cttataaaaa acccgcgtt ctgcaaacct  120
ttctcgataa aagtgacaac cactgagtaa acagatcaat ggaagtaaat tccaattgtt  180
tattggattt gcccctatat ttccagacat ctgttatcac ttaacccatt acaagcccgt  240
tgccgcagat attccgtgg cgagcgataa cccagcgcac tatgcggatg ccattcgtta  300
taatgctcga acgcctctgc aaggttcttt gctgccgtta acccgtctgg tttgggcatg  360
atactgatgt agtcacgctt tatcgttttc acgaagctct ctgctattcc gttactctcc  420
ggactccgca ccgccgtgtt cttcggttc                                    449
```

What is claimed is:

1. A method for storing data, the method comprising:
providing a register comprising a double-stranded deoxyribonucleic acid (DNA) sequence, wherein the DNA sequence has a plurality of nickable positions;
translating the data into a sequence of values from a nick alphabet, wherein the nick alphabet comprises at least a first value and a second value, wherein the first value indicates not to nick the DNA sequence, wherein the second value indicates to nick the DNA sequence, and wherein the sequence of values includes at least one second value;
mapping the sequence of values to the plurality of nickable positions; and
nicking one strand of the DNA sequence at each nickable position having a mapped value that indicates to nick the DNA sequence in order to provide an encoded register.

2. A method according to claim 1, wherein the second value indicates to nick a first strand of the DNA sequence.

3. A method according to claim 2, wherein:
the nick alphabet further comprises a third value; and
the third value indicates to nick a second strand of the DNA sequence.

4. A method according to claim 1, wherein each nickable position is individually associated with a nucleotide subsequence that is unique within the DNA sequence.

5. A method according to claim 4, wherein each unique subsequence comprises at least 12 nucleotides, at least 14 nucleotides, or at least 16 nucleotides.

6. A method according to claim 4, wherein 10% to 70%, or 20% to 60%, or 30% to 50% of each unique subsequence is guanine or cytosine.

7. A method according to claim 1, wherein any pair of nickable positions are separated in the DNA sequence by at least 16 nucleotides, at least 20 nucleotides, or at least 24 nucleotides.

8. A method according to claim 1, wherein the register comprising the DNA sequence comprises a plurality of DNA sequences, wherein each DNA sequence of the plurality is distinct, and wherein each DNA sequence has a plurality of respective nickable positions.

9. A method according to claim 1, wherein nicking one strand of the DNA sequence comprises cleaving the strand with an RNA- or DNA-programmable endonuclease.

10. A method according to claim 9, wherein the DNA-programmable endonuclease comprises a polypeptide having at least 50% sequence identity to the amino acid sequence set forth in SEQ ID NO:1.

11. A method according to claim 1, wherein the DNA sequence has at least 80% sequence identity to a nucleotide sequence native to a plant cell, a mammalian cell, an insect cell, a fungal cell, or a bacterial cell.

12. A method according to claim 11, wherein the DNA sequence has at least 80% sequence identity to a nucleotide sequence native to an *Escherichia coli* cell.

13. A method according to claim 1, wherein the nicking one strand of the DNA sequence comprises the nicking of a first nickable position and a second nickable position in parallel.

* * * * *